US012780887B2

(12) United States Patent
Kim et al.

(10) Patent No.: US 12,780,887 B2
(45) Date of Patent: Nov. 3, 2026

(54) MUTATION COMPLEX INCLUDING GAIN-OF-FUNCTION MUTANT OF BMPR2 GENE, INDUCED PLURIPOTENT STEM CELLS AND MESENCHYMAL STEM CELLS DERIVED FROM MUTANT, AND USE THEREOF

(71) Applicants: SOOKMYUNG WOMEN'S UNIVERSITY INDUSTRY-ACADEMIC COOPERATION FOUNDATION, Seoul (KR); SEOUL NATIONAL UNIVERSITY R&DB FOUNDATION, Seoul (KR)

(72) Inventors: Yonghwan Kim, Seoul (KR); Myung-Jin Kim, Seoul (KR); Tae Joon Cho, Seoul (KR)

(73) Assignees: SOOKMYUNG WOMEN'S UNIVERSITY INDUSTRY-ACADEMIC COOPERATION FOUNDATION, Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 889 days.

(21) Appl. No.: 18/011,419

(22) PCT Filed: Dec. 29, 2020

(86) PCT No.: PCT/KR2020/019327

§ 371 (c)(1),
(2) Date: Dec. 19, 2022

(87) PCT Pub. No.: WO2021/256647

PCT Pub. Date: Dec. 23, 2021

(65) Prior Publication Data

US 2023/0242605 A1 Aug. 3, 2023

(30) Foreign Application Priority Data

Jun. 19, 2020 (KR) ........................ 10-2020-0075327
Jun. 19, 2020 (KR) ........................ 10-2020-0075332

(51) Int. Cl.

| | |
|---|---|
| ***C07K 14/51*** | (2006.01) |
| ***A61K 35/28*** | (2015.01) |
| ***A61P 19/00*** | (2006.01) |
| ***C07K 14/71*** | (2006.01) |

(52) U.S. Cl.

CPC .............. *C07K 14/51* (2013.01); *A61K 35/28* (2013.01); *A61P 19/00* (2018.01); *C07K 14/71* (2013.01)

(58) Field of Classification Search
None
See application file for complete search history.

(56) References Cited

U.S. PATENT DOCUMENTS

| | | | | |
|---|---|---|---|---|
| 2004/0077043 A1* | 4/2004 | Watarai | ................ | C07K 14/705 435/325 |
| 2009/0029371 A1 | 1/2009 | Elliott | | |
| 2010/0151529 A1* | 6/2010 | Zhao | .................... | C12N 9/0004 435/320.1 |
| 2021/0061898 A1* | 3/2021 | Hatsell | .................... | A61P 19/08 |
| 2025/0333492 A1* | 10/2025 | Zhang | ...................... | A61P 35/00 |

FOREIGN PATENT DOCUMENTS

| | | |
|---|---|---|
| CN | 109266679 A | 1/2019 |

OTHER PUBLICATIONS

Eileen M. Shore et al., "Inherited human diseases of heterotopic bone formation", Nat Rev Rheumatol, Sep. 2010, pp. 518-527, vol. 6, No. 9.
Frederick S. Kaplan et al., "Fibrodysplasia ossificans progressiva", Best Practice & Research Clinical Rheumatology, 2008, pp. 191-205, vol. 22, No. 1.
O. Will Towler et al., "The congenital great toe malformation of fibrodysplasia ossificans progressiva?—A close call", European Journal of Medical Genetics, May 1, 2017, pp. 399-402.
Robert J Pignolo et al., "The Natural History of Flare-Ups in Fibrodysplasia Ossificans Progressiva (FOP): A Comprehensive Global Assessment", Journal of Bone and Mineral Research, Mar. 2016, pp. 650-656, vol. 31, No. 3.
Eileen M Shore et al., "A recurrent mutation in the BMP type I receptor ACVR1 causes inherited and sporadic fibrodysplasia ossificans progressiva", Nature Genetics, Apr. 23, 2006, pp. 525-528, vol. 38, No. 5.
Robert J. Pignolo et al., "Natural history of fibrodysplasia ossificans progressiva: crosssectional analysis of annotated baseline phenotypes", Orphanet Journal of Rare Diseases, May 3, 2019, pp. 1-11.
Julia Haupt et al., "Variable signaling activity by FOP ACVR1 mutations", Bone, Oct. 31, 2017, pp. 232-240.

(Continued)

*Primary Examiner* — Michail A Belyavskyi
(74) *Attorney, Agent, or Firm* — Paratus Law Group, PLLC

(57) ABSTRACT

There is provided a mutation complex including: a BMPR2-E376K mutant in which an amino acid at position 376 of BMPR2 gene encoding a bone morphogenetic protein type 2 receptor (BMPR2) has mutated from glutamic acid (E) to lysine (K); and an ACVR1-R206H mutant in which an amino acid at position 206 of ACVR1 gene encoding an activin A type I receptor (ACVR1) has mutated from arginine (R) to histidine (H). There are also provided induced pluripotent stem cells reprogrammed from cells including the BMPR2-E376K mutant in which an amino acid at position 376 of BMPR2 gene encoding a bone morphogenetic protein type 2 receptor (BMPR2) has mutated from glutamic acid (E) to lysine (K).

4 Claims, 34 Drawing Sheets

Specification includes a Sequence Listing.

(56) References Cited

OTHER PUBLICATIONS

Paul B Yu al., BMP type I receptor inhibition reduces heterotopic ossification, Nature Medicine, Nov. 30, 2008, pp. 1363-1370, vol. 14, No. 12.
Salin A Chakkalakal et al., “An Acvr1 R206H Knock-in Mouse Has Fibrodysplasia Ossificans Progressiva”, Journal of Bone and Mineral Research, Apr. 16, 2012, pp. 1746-1756, vol. 27, No. 8.
Andria L. Culbert et al., “Alk2 Regulates Early Chondrogenic Fate in Fibrodysplasia Ossificans Progressiva Heterotopic Endochondral Ossification”, Stem Cells, May 2014, pp. 1289-1300.
Sarah J. Hatsell et al., “ACVR1R206H receptor mutation causes fibrodysplasia ossificans progressiva by imparting responsiveness to activin A”, Sci Transl Med, Sep. 2, 2015, pp. 1-23.
Kyosuke Hino et al., “Neofunction of ACVR1 in fibrodysplasia ossificans progressiva”, PNAS, Dec. 15, 2015, pp. 15438-15443, vol. 112, No. 50.
Rajiv D. Machado et al., “Pulmonary Arterial Hypertension: A Current Perspective on Established and Emerging Molecular Genetic Defects”, Human Mutation, Sep. 21, 2015, pp. 1113-1127, vol. 36, No. 12.
Yinxiang Wang et al., “Reprogramming of Dermal Fibroblasts into Osteo-Chondrogenic Cells with Elevated Osteogenic Potency by Defined Transcription Factors”, Stem Cell Reports, Jun. 6, 2017, pp. 1587-1599, vol. 8.
Vonda J. Wright et al., “BMP4-Expressing Muscle-Derived Stem Cells Differentiate into Osteogenic Lineage and Improve Bone Healing in Immunocompetent Mice”, Molecular Therapy, Aug. 2002, pp. 169-178, vol. 6, No. 2.
Kenta Yamamoto et al., “Direct conversion of human fibroblasts into functional osteoblasts by defined factors”, PNAS, May 12, 2015, pp. 6152-6157, vol. 112, No. 19.
Roland Takács et al., “Comparative Analysis of Osteogenic/Chondrogenic Differentiation Potential in Primary Limb Bud-Derived and C3H10T1/2 Cell Line-Based Mouse Micromass Cultures”, International Journal of Molecular Sciences, Aug. 5, 2013, pp. 16141-16167.
Siim Pauklin et al., “Activin/Nodal signalling in stem cells”, Development, 2015, pp. 607-619.
Maria Namwanje et al., “Activins and Inhibins: Roles in Development, Physiology, and Disease”, Cold Spring Harbor Perspectives in Biology, Jun. 21, 2016, pp. 1-55.
Gregory J Anderson et al., “Small-molecule dissection of BMP signaling”, Nature Chemical Biology, Jan. 2008, pp. 15-16, vol. 4, No. 1.
Long Zhang et al., “Signaling interplay between transforming growth factor-β receptor and PI3K/AKT pathways in cancer”, Trends in Biochemical Sciences, Dec. 2013, pp. 612-620, vol. 38, No. 12.
Laura Southgate et al., “Molecular genetic framework underlying pulmonary arterial hypertension”, Nature Reviews Cardiology, Aug. 12, 2019, pp. 1-11.
Myung-Jin Kim et al., “Clinical significance linked to functional defects in bone morphogenetic protein type 2 receptor, BMPR2”, BMB Reports, 2017, pp. 308-317.
Rachel K. Hopper et al., “In Pulmonary Arterial Hypertension, Reduced BMPR2 Promotes Endothelial-to-Mesenchymal Transition via HMGA1 and Its Target Slug”, Circulation, May 3, 2016, pp. 1783-1794.
Xiao Wang et al., “Inhibition of overactive TGF-β attenuates progression of heterotopic ossification in mice”, Nature Communications, Feb. 7, 2018, pp. 1-13.
Hae Ryung Chang et al., “Hypomorphic Mutations in TONSL Cause Sponastrime Dysplasia”, The American Journal of Human Genetics, Mar. 7, 2019, pp. 439-453.
Heng Li et al., “Fast and accurate short read alignment with Burrows-Wheeler transform” Bioinformatics, May 18, 2009, pp. 1754-1760, vol. 25, No. 14.
Heng Li et al., “The Sequence Alignment/Map format and SAMtools”, Bioinformatics, Jun. 8, 2009, pp. 2078-2079, vol. 25, No. 16.
Aaron Mckenna et al., “The Genome Analysis Toolkit: A MapReduce framework for analyzing next-generation DNA sequencing data”, Genome Research, Jul. 19, 2010, pp. 1297-1303.
Kai Wang et al., “ANNOVAR: functional annotation of genetic variants from high-throughput sequencing data”, Nucleic Acids Research, Jul. 3, 2010, pp. 1-7, vol. 38, No. 16.
Sue Richards et al., “Standards and guidelines for the interpretation of sequence variants: a joint consensus recommendation of the American College of Medical Genetics and Genomics and the Association for Molecular Pathology”, Genetics in Medicine, Mar. 5, 2015, pp. 405-424, vol. 17, No. 5.
International Search Report for PCT/KR2020/019327 mailed Apr. 13, 2021 from Korean Intellectual Property Office.
Gonzalo Sanchez-Duffhues et al., “Bone morphogenetic protein receptors: Structure, function and targeting by selective small molecule kinase inhibitors”, Bone, Jun. 6, 2020, pp. 1-13, vol. 138, No. 115472.
Rozenn Quarck et al., “Rescuing BMPR2-driven endothelial dysfunction in PAH: a novel treatment strategy for the future?”, Stem Cell Investigation, Jun. 14, 2017, pp. 1-3, vol. 4, No. 56.
Robert J. Pignolo et al., “Correction to: Natural history of fibrodysplasia ossificans progressiva: crosssectional analysis of annotated baseline phenotypes”, Orphanet Journal of Rare Diseases, May 23, 2019, pp. 1-2.

* cited by examiner

Sporadic (*de novo*)

FIG. 1e

| | 361 380 | |
|---|---|---|
| Patient | NRLVRPGEED NAAISKVGTI | → SEQ ID No. 41 |
| *Homo sapiens* | NRLVRPGEED NAAISEVGTI | → SEQ ID No. 42 |
| *Mus musculus* | NRLVRPGEED NAAISEVGTI | → SEQ ID No. 43 |
| *Rattus norvegicus* | NRLVRPGEED NAAISEVGTI | → SEQ ID No. 44 |
| *Bos taurus* | NRLVRPGEED NAAISEVGTI | → SEQ ID No. 45 |
| *Gallus gallus* | NRLVRPGEED NAAISEVGTI | → SEQ ID No. 46 |
| *Callithrix jacchus* | NRLVRPGEED NAAISEVGTI | → SEQ ID No. 47 |
| *Sus scrofa* | NRLVRPGEED NAAISEVGTI | → SEQ ID No. 48 |

FIG. 1f

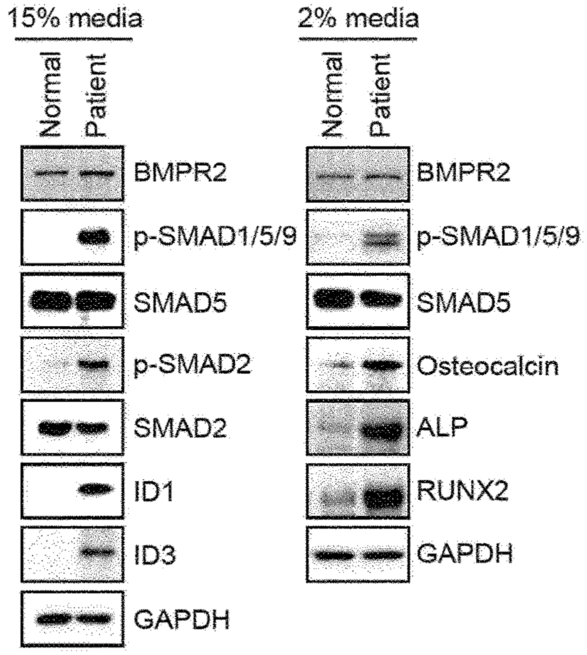

MUTATION COMPLEX INCLUDING GAIN-OF-FUNCTION MUTANT OF BMPR2 GENE, INDUCED PLURIPOTENT STEM CELLS AND MESENCHYMAL STEM CELLS DERIVED FROM MUTANT, AND USE THEREOF

ACKNOWLEDGEMENT

The present invention was made with the support of the Korean Ministry of Science, ICT & Future Planning in 2020, under Project No. 1711043428, which was conducted in the research project "Identification of Pathogenesis through the Study of Biological Functions of Genes Causing Rare and Intractable Skeletal Disorders" within the project "Genome Future Source Technology Development Pilot Project," with the support of the Korean Ministry of Science and ICT in 2020, under Project No. 1711112814, which was conducted in the research project "Research on the Function of TONSL Complexes in the Process of DNA Damage Repair and DNA Replication" within the project "(Type 1-2) Mid-level Research (within an average annual research cost of 100 to 200 million won)," and with the support of the Korean Ministry of Science and ICT in 2020, under Project No. 1711105488, which was conducted in the research project "Cellular Heterogeneity Research Center" within the project "Science and Engineering Technology Sector (S/ERC)."

CROSS-REFERENCE TO RELATED APPLICATIONS

This application is a National Stage Patent Application of PCT International Patent Application No. PCT/KR2020/019327 (filed on Dec. 29, 2020) under 35 U.S.C. § 371, which claims priority to Korean Patent Application Nos. 10-2020-0075332 (filed on Jun. 19, 2020) and 10-2020-0075327 (filed on Jun. 19, 2020), which are all hereby incorporated by reference in their entirety.

SEQUENCE LISTING

This application contains a Sequence Listing submitted via EFS-Web and hereby incorporated by reference in its entirety. The Sequence Listing is named "Updated_Sequence_Listing.txt", created on Apr. 20, 2026, and 24,294 bytes in size.

BACKGROUND

The present invention relates to a novel mutant and a use thereof, and more specifically, to a mutant complex including a gain-of-function mutant in the BMPR2 gene derived from a patient with Fibrodysplasia ossificans progressiva (FOP), induced pluripotent stem cells and mesenchymal stem cells derived from the mutant, and a use thereof.

Fibrodysplasia ossificans progressiva (FOP, MIM #135100) is a rare autosomal hereditary skeletal disorder characterized by progressive heterotopic bone formation in connective tissues, resulting in disabling conditions (see non-patent documents 1 and 2). A typical feature of patients presenting with FOP is the congenital malformation of a big toe (see non-patent documents 3) About 70% of FOP patients experience episodic pre-osseous inflammatory soft tissue swellings, known as flare-ups, which precede heterotopic ossification (see non-patent documents 4).

Understanding the molecular basis of FOP has been spurred by the identification of causative gain-of-function mutations of the gene encoding ACVR1, a type 1 TGF-beta receptor responsible for bone morphogenetic protein (BMP) signaling (see non-patent document 5). To date, a number of ACVR1 variants have been identified, although 95% of FOP cases are attributed to the ACVR1-R206H mutation (see non-patent documents 6 and 7).

Accumulated evidence supports the idea that the gain-of-function mutation in ACVR1 constitutively stimulates BMP signaling even in the absence of BMP ligands, leading to heterotopic ossifications (see non-patent documents 8 to 10). Interestingly, it was demonstrated that activin A, a cytokine antagonizing BMP signaling in a wild-type (WT) ACVR1 background, specifically enhances BMP signaling within cells harboring the ACVR1-R206H mutation (see non-patent documents 11 and 12). The involvement of activin A in FOP has been validated in the FOP mouse model by showing that treatment with an antibody against activin A reduces heterotopic bone formation (see non-patent document 11). The exact molecular basis of how activin A forces ACVR1 mutation-dependent hyperactivation of BMP signaling remains elusive. In addition, the limited amount of information about the genetic causes of FOP hampers our understanding of the pathophysiology of the disease.

Non-Patent Document

1. Shore E M, Kaplan F S. Inherited human diseases of heterotopic bone formation. Nat Rev Rheumatol 2010; 6:518-27.
2. Kaplan F S, Le Merrer M, Glaser D L, et al. Fibrodysplasia ossificans progressiva. Best Pract Res Clin Rheumatol 2008; 22:191-205.
3. Towler O W, Shore E M, Xu M, et al. The congenital great toe malformation of fibrodysplasia ossificans progressiva?—A close call. Eur J Med Genet 2017; 60:399-402.
4. Pignolo R J, Bedford-Gay C, Liljesthrom M, et al. The Natural History of Flare-Ups in Fibrodysplasia Ossificans Progressiva (FOP): A Comprehensive Global Assessment. J Bone Miner Res 2016; 31:650-6.
5. Shore E M, Xu M, Feldman G J, et al. A recurrent mutation in the BMP type I receptor ACVR1 causes inherited and sporadic fibrodysplasia ossificans progressiva. Nat Genet 2006; 38:525-7.
6. Pignolo R J, Baujat G, Brown M A, et al. Natural history of fibrodysplasia ossificans progressiva: cross-sectional analysis of annotated baseline phenotypes. Orphanet J Rare Dis 2019; 14:98.
7. Haupt J, Xu M, Shore E M. Variable signaling activity by FOP ACVR1 mutations. Bone 2018; 109:232-40.
8. Yu P B, Deng D Y, Lai C S, et al. BMP type I receptor inhibition reduces heterotopic [corrected] ossification. Nat Med 2008; 14:1363-9.
9. Chakkalakal S A, Zhang D, Culbert A L, et al. An Acvr1 R206H knock-in mouse has fibrodysplasia ossificans progressiva. J Bone Miner Res 2012; 27:1746-56.
10. Culbert A L, Chakkalakal S A, Theosmy E G, Brennan T A, Kaplan F S, Shore E M. Alk2 regulates early chondrogenic fate in fibrodysplasia ossificans progressiva heterotopic endochondral ossification. Stem Cells 2014; 32:1289-300.
11. Hatsell S J, Idone V, Wolken D M, et al. ACVR1R206H receptor mutation causes fibrodysplasia ossificans progressiva by imparting responsiveness to activin A. Sci Transl Med 2015; 7:303ra137.
12. Hino K, Ikeya M, Horigome K, et al. Neofunction of ACVR1 in fibrodysplasia ossificans progressiva. Proc Natl Acad Sci USA 2015; 112:15438-43.

13. Machado R D, Southgate L, Eichstaedt C A, et al. Pulmonary Arterial Hypertension: A Current Perspective on Established and Emerging Molecular Genetic Defects. Hum Mutat 2015; 36:1113-27.
14. Wang Y, Wu M H, Cheung M P L, et al. Reprogramming of Dermal Fibroblasts into Osteo-Chondrogenic Cells with Elevated Osteogenic Potency by Defined Transcription Factors. Stem Cell Reports 2017; 8:1587-99.
15. Wright V, Peng H, Usas A, et al. BMP4-expressing muscle-derived stem cells differentiate into osteogenic lineage and improve bone healing in immunocompetent mice. Mol Ther 2002; 6:169-78.
16. Yamamoto K, Kishida T, Sato Y, et al. Direct conversion of human fibroblasts into functional osteoblasts by defined factors. Proc Natl Acad Sci USA 2015; 112:6152-7.
17. Takacs R, Matta C, Somogyi C, Juhasz T, Zakany R. Comparative analysis of osteogenic/chondrogenic differentiation potential in primary limb bud-derived and C3H10T1/2 cell line-based mouse micromass cultures. Int J Mol Sci 2013; 14:16141-67.
18. Pauklin S, Vallier L. Activin/Nodal signalling in stem cells. Development 2015; 142:607-19.
19. Namwanje M, Brown C W. Activins and Inhibins: Roles in Development, Physiology, and Disease. Cold Spring Harb Perspect Biol 2016; 8.
20. Anderson G J, Darshan D. Small-molecule dissection of BMP signaling. Nat Chem Biol 2008; 4:15-6.
21. Zhang L, Zhou F, ten Dijke P. Signaling interplay between transforming growth factor-beta receptor and PI3K/AKT pathways in cancer. Trends Biochem Sci 2013; 38:612-20.
22. Southgate L, Machado R D, Graf S, Morrell N W. Molecular genetic framework underlying pulmonary arterial hypertension. Nat Rev Cardiol 2019.
23. Kim M J, Park S Y, Chang H R, et al. Clinical significance linked to functional defects in bone morphogenetic protein type 2 receptor, BMPR2. BMB Rep 2017; 50:308-17.
24. Hopper R K, Moonen J R, Diebold I, et al. In Pulmonary Arterial Hypertension, Reduced BMPR2 Promotes Endothelial-to-Mesenchymal Transition via HMGA1 and Its Target Slug. Circulation 2016; 133:1783-94.
25. Wang X, Li F, Xie L, et al. Inhibition of overactive TGF-beta attenuates progression of heterotopic ossification in mice. Nat Commun 2018; 9:551.
26. Chang H R, Cho S Y, Lee J H, et al. Hypomorphic Mutations in TONSL Cause SPONASTRIME Dysplasia. Am J Hum Genet 2019; 104:439-53.
27. Li H, Durbin R. Fast and accurate short read alignment with Burrows-Wheeler transform. Bioinformatics 2009; 25:1754-60.
28. Li H, Handsaker B, Wysoker A, et al. The Sequence Alignment/Map format and SAMtools. Bioinformatics 2009; 25:2078-9.
29. McKenna A, Hanna M, Banks E, et al. The Genome Analysis Toolkit: a MapReduce framework for analyzing next-generation DNA sequencing data. Genome Res 2010; 20:1297-303.
30. Wang K, Li M, Hakonarson H. ANNOVAR: functional annotation of genetic variants from high-throughput sequencing data. Nucleic Acids Res 2010; 38:e164.
31. Richards S, Aziz N, Bale S, et al. Standards and guidelines for the interpretation of sequence variants: a joint consensus recommendation of the American College of Medical Genetics and Genomics and the Association for Molecular Pathology. Genet Med 2015; 17:405-24.

SUMMARY

The present invention relates to a novel case of the FOP-like phenotype in addition to the existing ACVR1-R206H mutation, which is known to cause FOP, and is to present a technology in which a mutation of a specific gene is found and can be utilized to treat bone disease through osteogenic differentiation.

In addition, the present invention is to present a technology in which the effect when the mutant is bound and expressed with the existing ACVR1-R206H mutation is identified and this can be utilized to treat bone disease through osteogenic differentiation.

In a first aspect for solving the problem above, the present invention provides a mutation complex including a BMPR2-E376K mutant in which an amino acid 376 of a bone morphogenetic protein type 2 receptor (BMPR2) gene encoding BMPR2 is mutated from glutamic acid (E) to lysine (K) and an ACVR1-R206H mutant in which an amino acid 206 of an activin A type I receptor (ACVR1) gene encoding ACVR1 is mutated from arginine (R) to histidine (H).

In addition, there is provided the mutation complex characterized by having an additive effect to osteogenic differentiation by binding and expressing the BMPR2-E376K mutant and the ACVR1-R206H mutant.

In addition, there is provided the mutation complex characterized by being used to treat bone disease through osteogenic differentiation.

In a second aspect for solving the problem above, the present invention provides a cell line including the mutant.

In a third aspect for solving the problem above, the present invention provides induced pluripotent stem cells reprogrammed from cells containing a BMPR2-E376K mutant in which an amino acid 376 of a bone morphogenetic protein type 2 receptor (BMPR2) gene encoding BMPR2 is mutated from glutamic acid (E) to lysine (K).

In addition, there is provided the induced pluripotent stem cells characterized in that the mutant has a point mutation of guanine (G) to adenine (A) at nucleotide 1126.

In addition, there is provided the induced pluripotent stem cells characterized in that the mutant causes a phenotype of Fibrodysplasia ossificans progressiva (FOP).

In a fourth aspect for solving the problem above, the present invention provides mesenchymal stem cells differentiated from the induced pluripotent stem cells.

In addition, there is provided the induced pluripotent stem cells characterized in that the mesenchymal stem cells are used to treat bone disease through osteogenic differentiation.

In a fifth aspect for solving the problem above, the present invention provides a method for screening a drug for treating bone disease by applying a candidate drug to the mesenchymal stem cells.

The present invention relates to a novel case of the FOP-like phenotype. The patient developed flare-ups and heterotopic bone formation throughout the body, which is similar to the phenotype of the ACVR1 mutation. However, the proband does not have big toe anomaly or any mutation in the ACVR1 gene. From whole exome sequencing, the present inventors identified and functionally validated a causative gain-of-function mutation in the bone morphogenetic protein type 2 receptor (BMPR2) gene, which encodes a type II TGF-beta receptor in the BMP signaling cascade. This is the first report of a BMPR2 gain-of-function mutation and the resultant FOP-like phenotype. Identification of additional genetic alterations leading to the FOP-like phenotype will be informative regarding the molecular basis of the disease and the biology of TGF/BMP signaling in general.

Meanwhile, in the present invention, additional genetic mutations showing a FOP-like phenotype have been found, and reprogrammed induced pluripotent stem cells including the BMPR2-E376K mutant and mesenchymal stem cells differentiated from the induced pluripotent stem cells can be differentiated into various tissue cells, and this technique can not only be utilized to treat bone disease through osteogenic differentiation, but can also prepare the ground for screening a therapeutic agent for treating bone disease.

BRIEF DESCRIPTION OF THE DRAWINGS

FIGS. 1*a* to 1*h* are photos and graphs related to the Identification of a novel variant in a patient with FOP.

FIG. 1*a* shows radiographs of the proband at age 16 years. Arrows denote the ectopic bone formation in the skeletal muscle. Unlike the typical FOP patient, he has no big toe anomaly.

FIG. 1*b* is the pedigree chart of the BMPR2 variant in the family. The arrow indicates the proband.

FIG. 1*c* shows whole exome sequencing detected a heterozygous de novo missense mutation in the BMPR2 gene. The proband has a point mutation of guanine (G) to adenine (A) at nucleotide 1126.

FIG. 1*d* is schematic of functional domains and the site of mutation in the BMPR2 protein. The mutation is within exon 8 in the kinase domain (KD) of BMPR2™, transmembrane; ECD, extracellular domain; CTD, C-terminal domain.

FIG. 1*e* shows the interspecies homology of the kinase domain of BMPR2. The conserved sequence is indicated by gray shading and the E376K variant is red.

In FIG. 1*f*, expression of SMAD signaling (p-SMAD1/5/9, SMAD5, p-SMAD2, SMAD2), its downstream target genes (ID1, ID3), and osteogenic differentiation markers (osteocalcin, ALP, RUNX2) in normal (BJ fibroblast) and FOP patient cells were examined by western blotting. Normal and patient cells were cultured under complete media (15% serum) or low serum media (2% horse serum) for inducing osteogenic differentiation.

FIG. 1*g* shows alkaline phosphatase (ALP) staining (left panel) of the normal and patient fibroblasts after differentiation induced by BMP2 or BMP4 (50 ng/ml) for 2 days. ALP is detected as purple color. ALP activity (right panel) was evaluated by measuring absorbance at 405 nm and total protein was measured using a Micro-BCA protein assay kit and read at 560 nm. The ALP activity was normalized to the protein content of the samples.

FIG. 1*h* shows Alizarin Red S staining indicative of calcium deposits in cells.

FIG. 2*a* is schematic of the human BMPR2 gene, showing the G1126A mutation in exon 8 (asterisk and underline). The G-to-A change leads to glutamic acid (upper line)-to-lysine (underline) mutation in the protein sequence. In clones corrected by CRISPR-Cas9, knock-out #3 had a 1 base pair (bp) deletion (hyphen) at nucleotide 1122, with the alleles in a 1:1 ratio. This resulted in a STOP signal. Knock-out #5 had a 1 bp insertion of nucleotide A (double underline), causing a STOP codon mutation. Finally, knock-in #203 contained a normal nucleotide guanine at 1126 and a CTC sequence from the HDR donor template, which preserved the WT amino acid sequence.

FIG. 2*b* shows protein expression determined by immunoblotting the lysates of the knock-out (#3 and #5) and knock-in (#203) clones edited by CRISPR-Cas9 in patient-derived dermal fibroblasts.

FIG. 2*c* shows western blot analysis to validate change of BMP signaling by BMPR2-E376K variant in HEK293T cells. HEK293T cells were transiently transfected with constructs expressing empty vector (EV), wild-type (WT), and mutant (mut) versions of BMPR2 (E376K) and ACVR1 (R206H) and then protein expression in the cell lysates was detected by immunoblotting.

FIG. 2*d* shows the promoter reporter assay in which luciferase expression is regulated by BMP-responsive elements in HEK293T cells transfected with plasmids carrying WT and mutant (mut) BMPR2 and ACVR1.

In FIG. 2*e*, C3H10T1/2 cells were transfected with empty vector (EV) or HA-tagged WT or mutant BMPR2 and their lysates examined for enhanced phosphorylation of SMAD1/5/9 and expression of downstream effectors ID1, ID3, and SOX9 by western blot analysis. The asterisk indicates a cross-reactive artifact.

FIG. 2*f* shows Alcian blue staining to detect chondrogenic capacity in C3H10T1/2 cells expressing BMPR2-WT or BMPR2-E376K under BMP2 treatment for 3 weeks. Quantification of staining was determined by measuring absorption at 600 nm.

FIG. 2*g* shows the mRNA expression of Col2a1, Aggrecan, and Col10al obtained from C3H10T1/2 cells expressing empty vector (EV), BMPR2-WT, or BMPR2-E376K, as analyzed by real-time PCR.

FIG. 3*a* shows the co-immunoprecipitation of HA-tagged BMPR2-E376K with wild-type (WT) V5-tagged ACVR1.

FIG. 3*b* shows the additive effect of both ACVR1-R206H and BMPR2-E376K in enhancing BMP signaling, as assessed by western blotting for p-SMAD1/5/9, p-SMAD2, ID1, and ID3.

FIG. 3*c* shows that phosphorylation of SMAD1/5/9 and SMAD2 increased upon treatment with activin A (50 ng/ml) in HEK293T cells expressing empty vector (EV) or V5-tagged WT or mutant (mut) BMPR2.

FIG. 3*d* shows the western blot analysis of phosphorylation of SMAD2 in HEK293T cells expressing V5-tagged WT or mutant (mut) ACVR1 or BMPR2.

FIG. 3*e* shows expression and phosphorylation of SMAD in the presence of siRNA against type I receptors, ALK2 or ALK5, in patient-derived dermal fibroblasts.

FIGS. 3*f* and 3*g* show ALP staining of C2C12 cell lines stably overexpressing HA-tagged WT or mutant (mut) BMPR2, with and without treatment with BMP4, dorsomorphin (DM), or SB431542 (SB).

FIG. 4*a* shows that HDR generates a specific single nucleotide modification by using a knockin donor template (120 mer) with synonymous mutations (CTC, underline) and wildtype G nucleotide (upper line).

FIG. 4*b* shows that NHEJ-mediated DSB repair frequently induces nucleotide insertions or deletions at the DSB site of BMPR2 mutant allele that causes amino acid insertions, deletions, or frameshift mutations leading to premature stop codons within the open reading frame of BMPR2 gene.

FIG. 4*c* shows that patterns of deep sequencing reads induced by sgRNA of BMPR2 mutant allele. The efficiency of HDR from the pool of deep sequencing reads was about 1.63%. Indels of the total reads were about 53.6%.

In FIG. 7*a*, HeLa and U20S cells stably expressing empty vector, HA-BMPR2-wildtype, or HA-BMPR2-mutant established by *lenti*-viral transduction were treated with siRNA for BMPR2 using a manner of reverse and forward transfection. Protein expression of SMAD1/5/9 phosphorylation from cell lysates was analyzed by western blotting. The asterisk indicates the cross-reacting band.

In FIG. 7*b*, HeLa and HEK293T cells expressing BMPR2 E376K variant were transfected with siRNA for ACVR1 (ALK2) or TGFBR1 (ALK5), a type I receptor and then phosphorylation of SMAD1/5/9 and SMAD2 were detected by western blotting.

In FIG. 8*a*, C2C12 cells stably expressing empty vector, HA-BMPR2-wildtype, or HA-BMPR2-mutant construct by *lenti*-viral transduction displayed protein expression for phosphorylation of SMAD1/5/9 and SMAD2 using western blotting, and in FIG. 8*b*, to differentiate from C2C12 cells to osteoblasts, cells were incubated in 2% low serum medium without or with BMP2 or BMP4 (50 ng/ml) at 37° C. with 5% $CO_2$. After 5 days, ALP staining was performed.

For quantitation of ALP activity, lysates from osteogenic differentiated cells for 5 days were incubated 0.67 M pNPP solution for 30 minutes at 37° C. and then the reaction was immediately followed by analyzing in absorbance at 405 nm.

Figure 9:
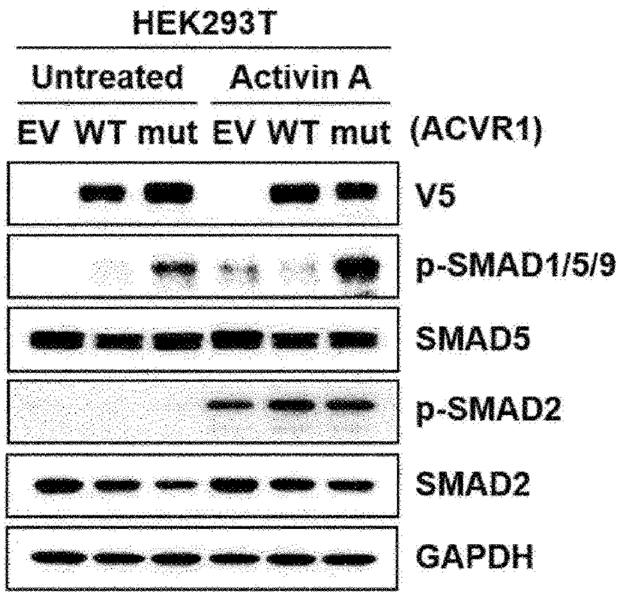

FIG. 9 is a photo showing protein level of SMAD phosphorylation by activin A treated in FOP causative mutant cells. HEK293T cells overexpressing empty vector, V5-ACVR1-wildtype, or V5-ACVR1 R206H were treated with activin A (50 ng/ml) for 5 minutes and then phosphorylation of SMAD1/5/9 and SMAD2 was confirmed through western blotting.

Figure 10:
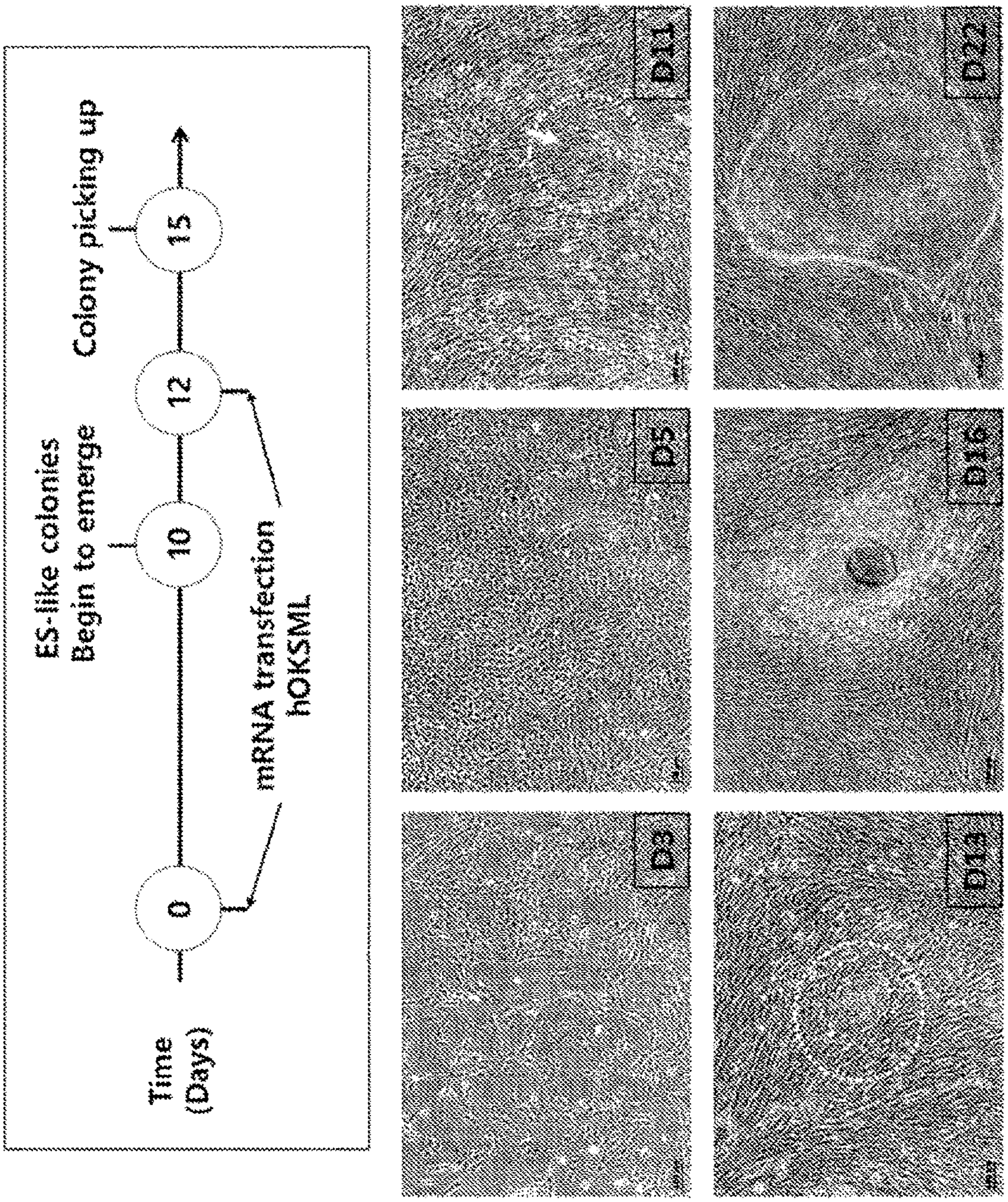

FIG. 10 shows images of cell colony and a schematic view illustrating a process of the generation of human induced pluripotent stem cells (hiPSCs) by the mRNA delivery.

Figure 11:
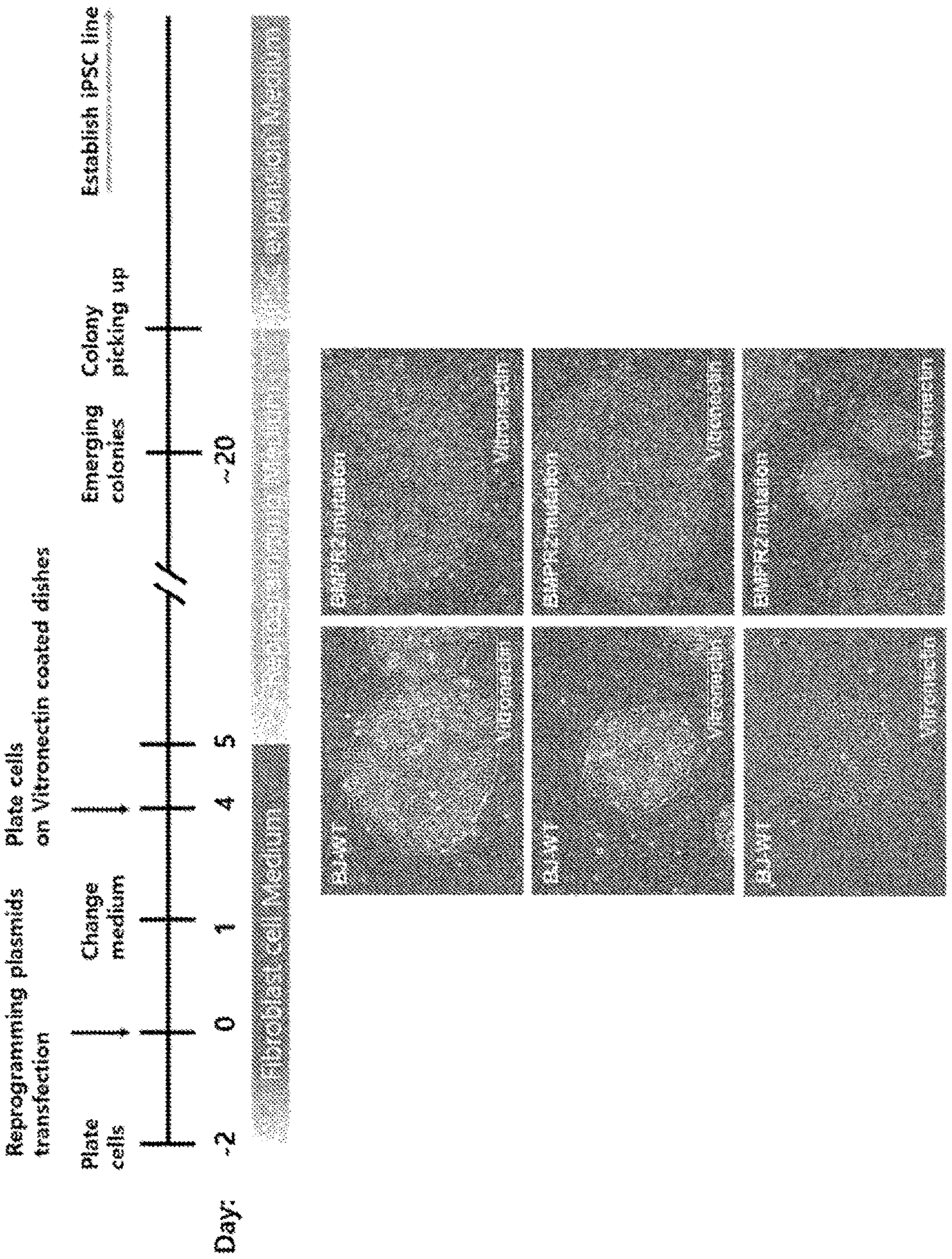

FIG. 11 shows images of forms of FOP-induced pluripotent stem cells and a schematic view illustrating a process of establishment of human induced pluripotent stem cells.

Figure 12:
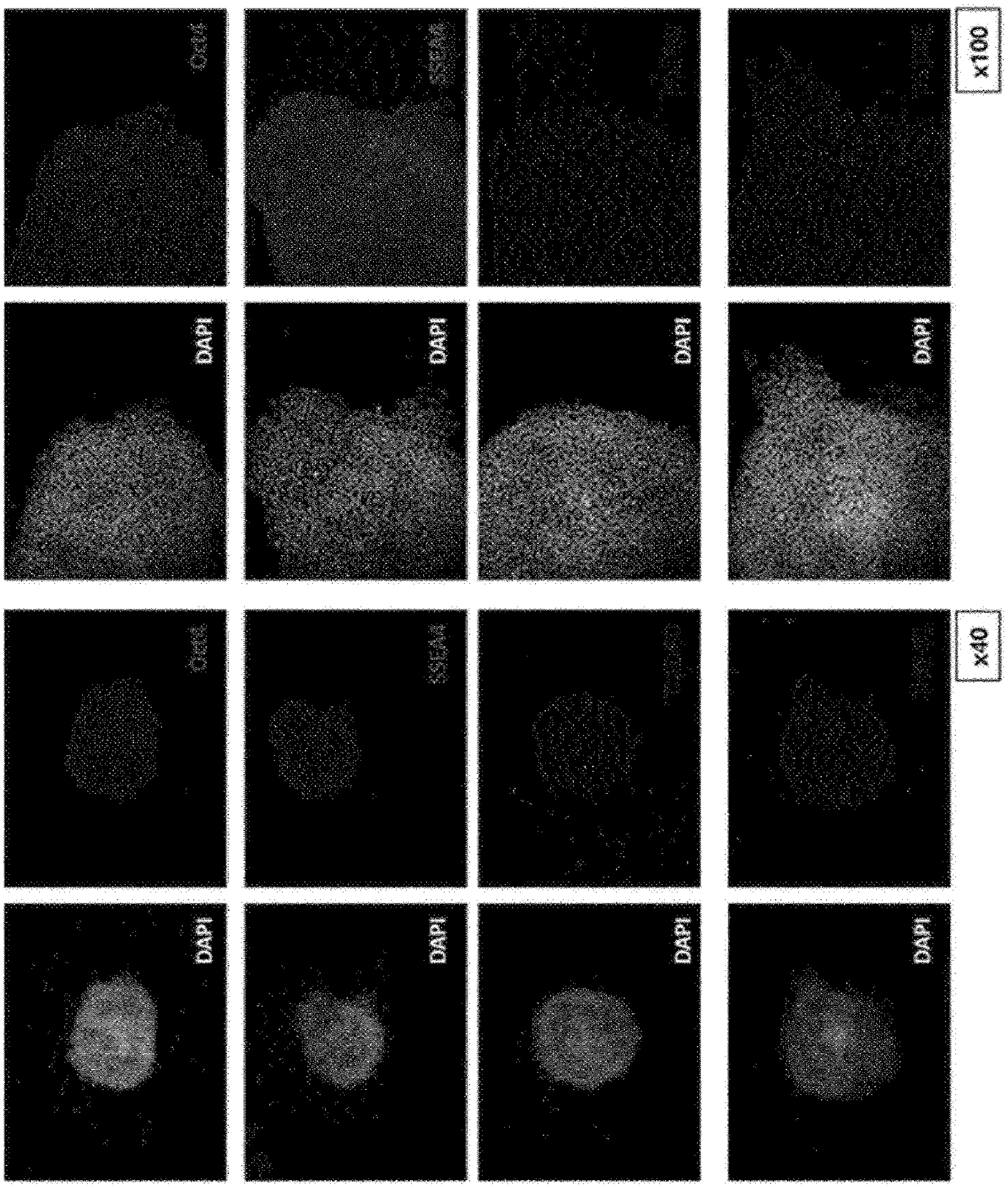

FIG. 12 shows photographs showing the results of immunofluorescence assay for verifying the presence of iPSs in the cell colony.

Figure 13:
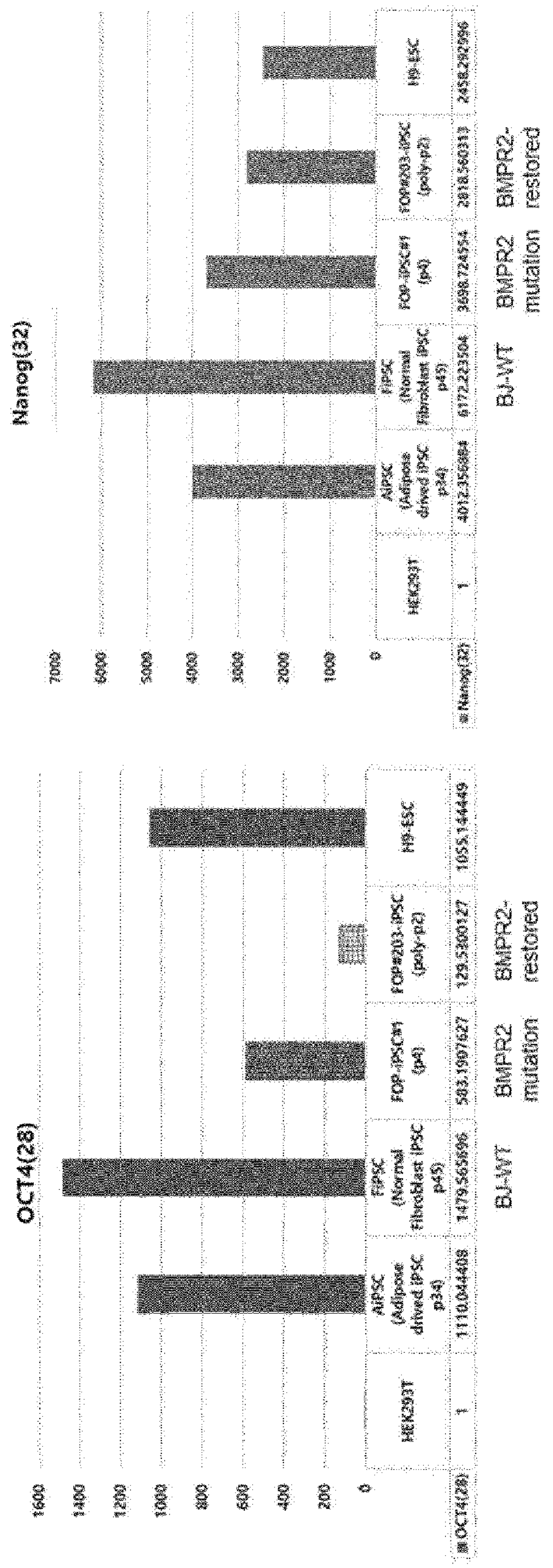

FIG. 13 shows graphs showing the results of mRNA expression of iPS markers (Oct 4 and Nanog) through qRT-PCR with respect to cDNA synthesized from each cell.

Figure 14:
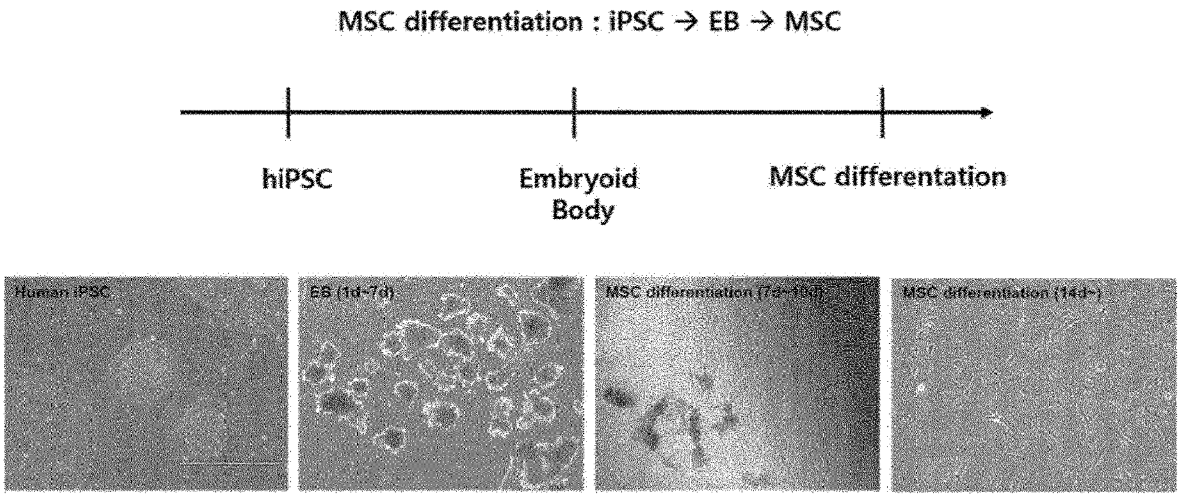

FIG. 14 shows images and a schematic view of a process of differentiation from iPSC to MSC.

Figure 15:
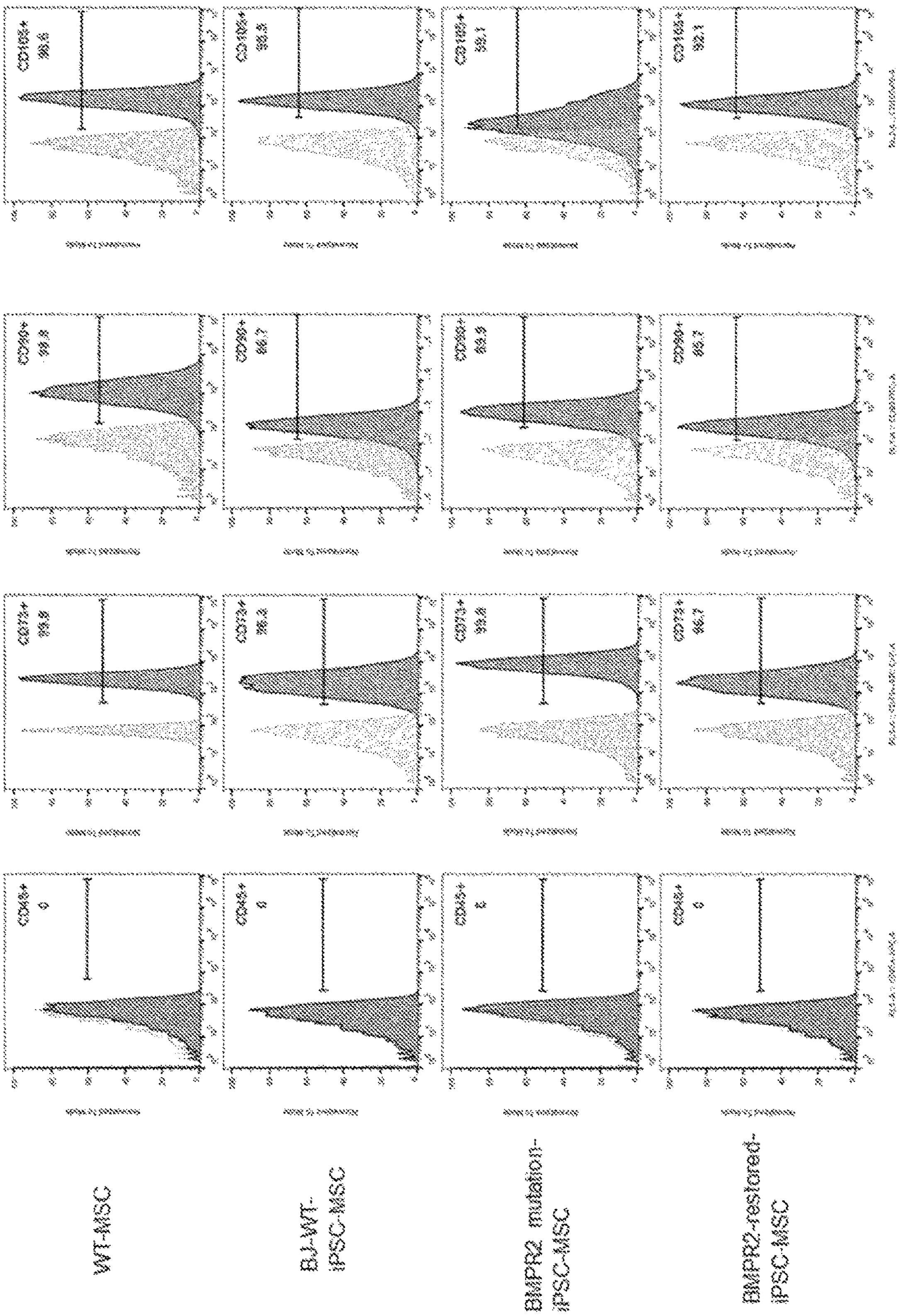

FIG. 15 shows graphs showing the results obtained by identifying the expression of MSC surface marker with a flow cytometry for verifying MSC.

Figure 16:
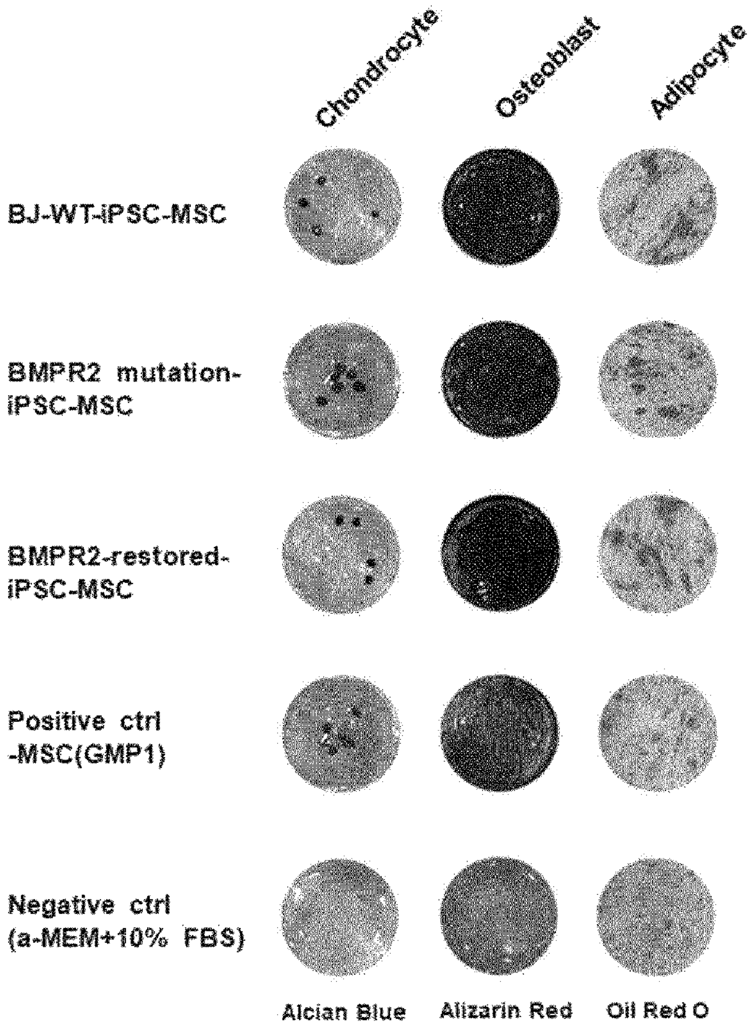

FIG. 16 shows photographs showing the results obtained by identifying the differentiation potential of MSCs through staining techniques by inducing the MSCs into chondrocytes, osteoblasts, and adipocytes.

Figure 17:
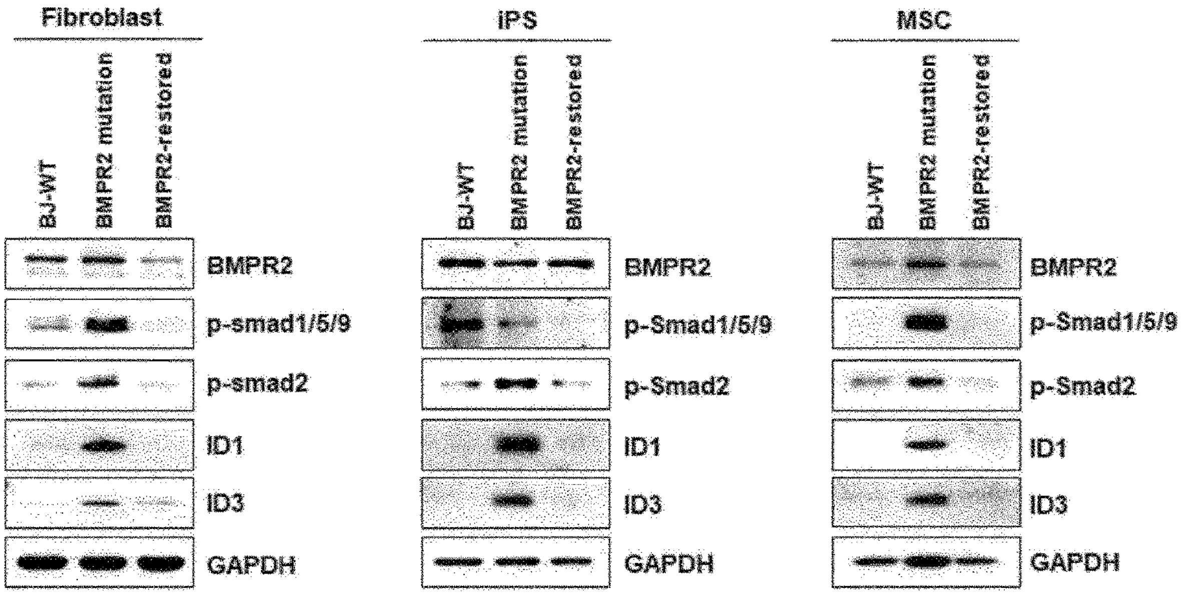

FIG. 17 shows images showing the results of the protein expression of BMP/SMAD signaling factors using iPSs and MSCs.

Figure 18:
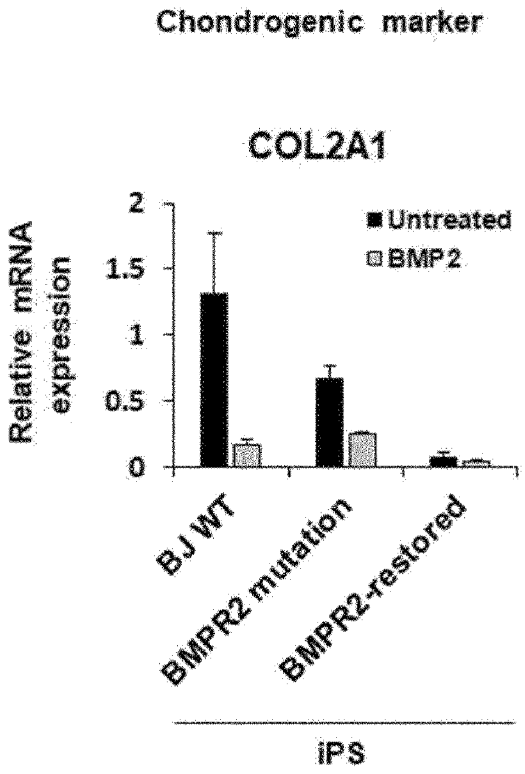

FIG. 18 is a graph showing the results of the expression of chondrogenic differentiation markers (Col2a1) of BJ-WT, BMPR2 mutation, and BMPR2-restored iPSs.

Figure 19:
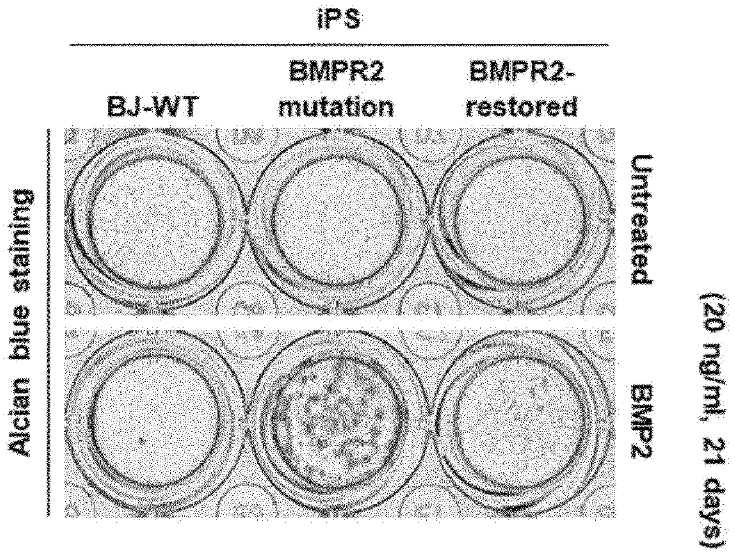

FIG. 19 is a photograph showing the results obtained by identifying chondrogenic differentiation levels using Alcian blue staining with respect to BJ-WT, BMPR2 mutation, and BMPR2-restored iPSs.

Figure 20:
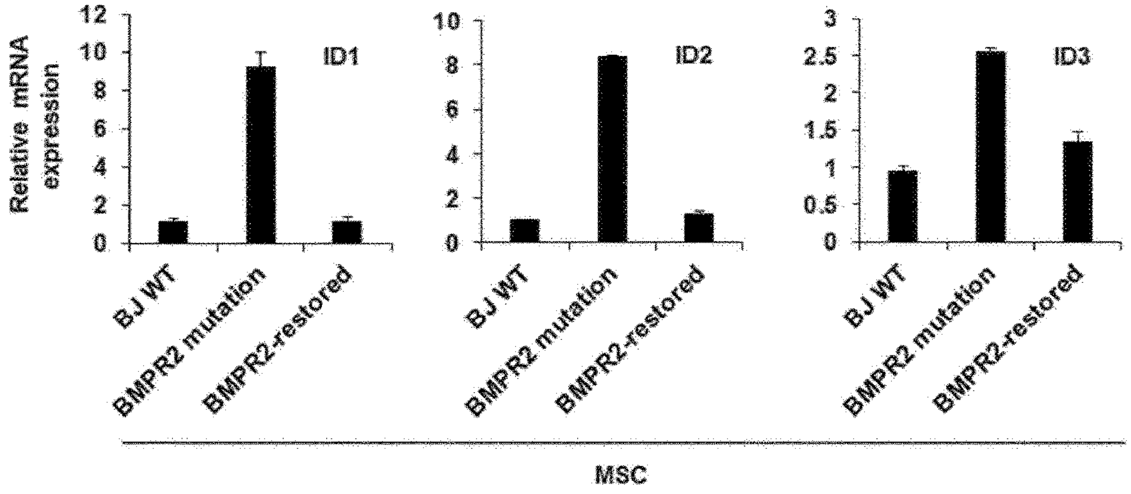

FIG. 20 shows graphs showing the results obtained by identifying, with qPCR, mRNA expression levels of BMP/SMAD1/5/9 target genes (ID1 to ID3) with respect to BJ-WT, BMPR2 mutation, and BMPR2-restored MSCs.

Figure 21:
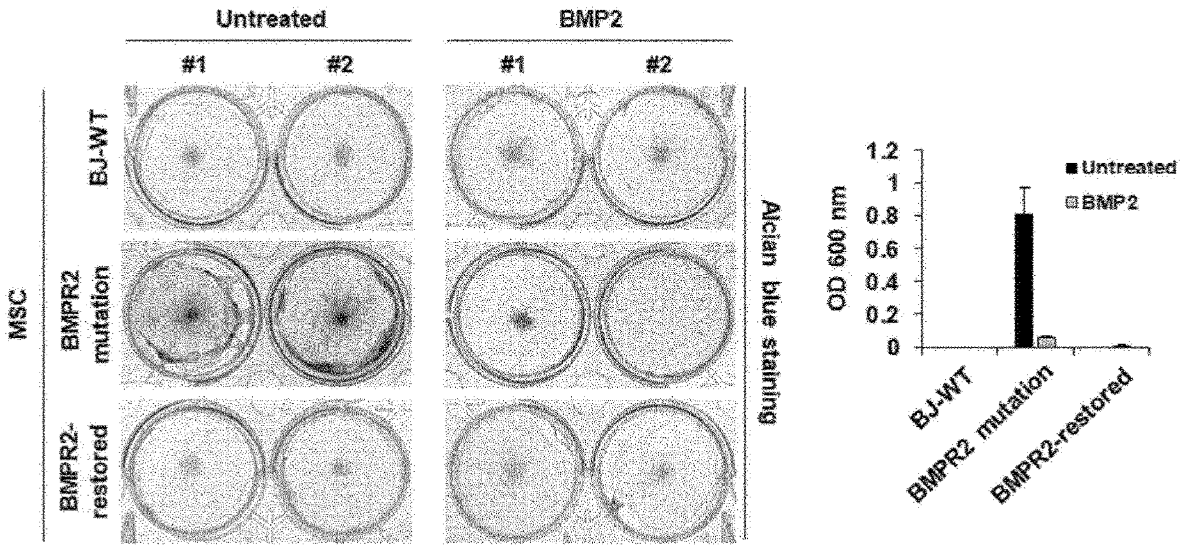

FIG. 21 shows photographs showing the results obtained by identifying chondrogenic differentiation levels using Alcian blue staining with respect to BJ-WT, BMPR2 mutation, and BMPR2-restored MSCs.

Figure 22:
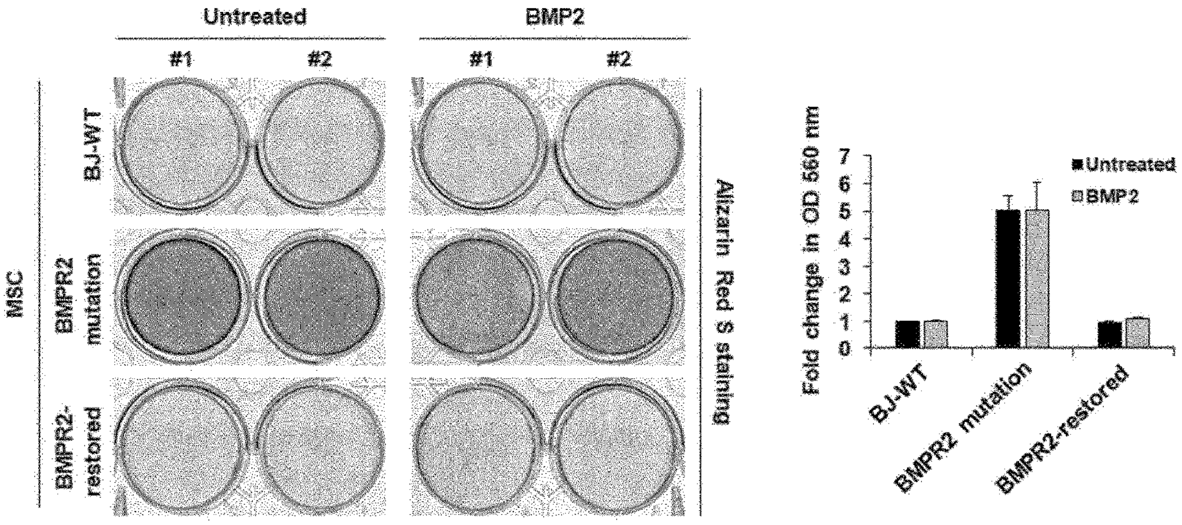

FIG. 22 shows photographs and a graph showing the results obtained by identifying calcium deposit levels using Alizarin Red S staining with respect to BJ-WT, BMPR2 mutation, and BMPR2-restored MSCs.

Figure 23:
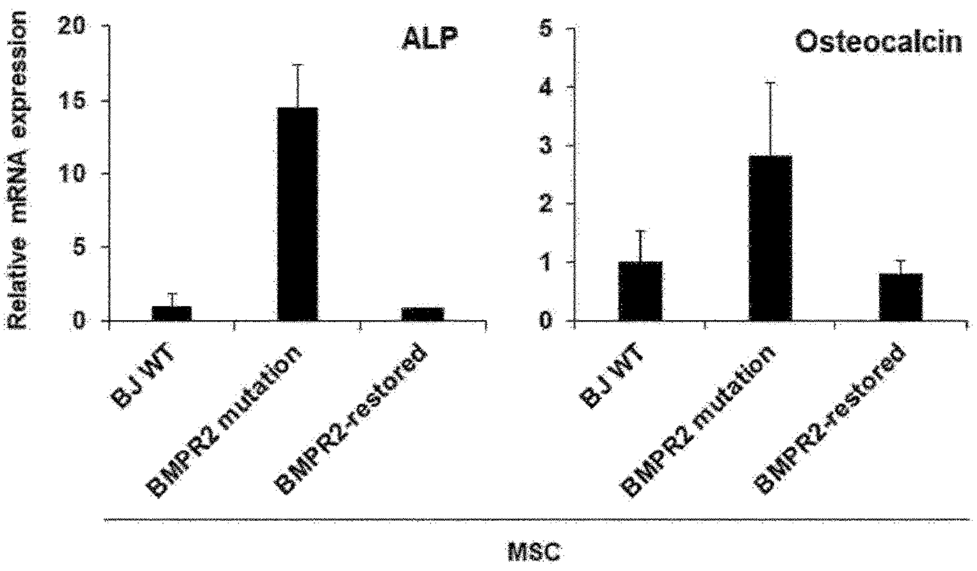

FIG. 23 shows graphs showing the results of mRNA expression of ALP and Osteocalcin of BJ-WT, BMPR2 mutation, and BMPR2-restored MSCs.

DETAILED DESCRIPTION

Hereinafter, preferred embodiments of the present invention will be described in detail. Before describing the present invention, it should be understood that the terms and words used in the specification and the appended claims should not be construed as limited to general and dictionary meanings but interpreted based on the meanings and concepts corresponding to technical aspects of the present invention on the basis of the principle that the inventor is allowed to define terms appropriately for the best explanation for the invention. Therefore, embodiments described in the specification and the example illustrated in the accompanying drawings herein is just a mere example for the purpose of illustrations only, not intended to represent all the technical aspects of the embodiment, the scope of the invention, so it should be understood that various equivalents and modifications thereof could be made at the time of filing.

Fibrodysplasia ossificans progressiva (FOP) is a rare autosomal dominant skeletal disorder characterized by progressive heterotopic ossification within soft connective tissues. All the patients presenting with clinical features of FOP so far have been identified to carry heterozygous gain-of-function mutations in the activin A type I receptor (ACVR1) gene.

With respect to this, the present invention presents a gain-of-function mutation in a bone morphogenetic protein type 2 receptor (BMPR2) gene encoding BMPR2 in a patient with a FOP-like phenotype, and furthermore, it is confirmed that binding and expression of the existing ACVR1 gene mutant and the novel BMPR2 gene mutant exhibits additive effects to the enhancement of SMAD1/5/9 phosphorylation and BMP signaling.

Therefore, the present invention presents a mutation complex including a BMPR2-E376K mutant in which an amino acid 376 of a bone morphogenetic protein type 2 receptor (BMPR2) gene encoding BMPR2 is mutated from glutamic acid (E) to lysine (K) and an ACVR1-R206H mutant in which an amino acid 206 of an activin A type I receptor (ACVR1) gene encoding ACVR1 is mutated from arginine (R) to histidine (H).

A 16-year-old boy had subcutaneous migrating modules on the scalp at age 3 and developed a series of flare-ups and subsequent soft tissue ossification initiated from the neck and back to the extremities starting at 6 years of age. Whole exome sequencing revealed a heterozygous de novo mutation of BMPR2, c.1126G>A (p.E376K), which was located in the highly conserved kinase domain of BMPR2. Constitutive activation of BMP signaling was detected in the patient-derived dermal fibroblasts, which was abrogated upon CRISPR/Cas9-mediated BMPR2 silencing. Consistently, ectopic expression of the BMPR2-E376K mutant in other cell lines induces SMAD1/5/9 phosphorylation, even in the absence of BMP ligands. At the cytological level, the patient-derived cells were positive for alkaline phosphatase expression and calcium accumulation, both of which were abolished by treatment with dorsomorphin, a BMP signaling inhibitor. These findings indicate that the BMPR2-E376K mutation causes a phenotype of progressive heterotopic ossification, similar to that of constitutively active ACVR1 mutation.

Hereinafter, the present invention will be described in detail with reference to Examples.

A Case of FOP

A 16-year-old boy presented with flare-ups of the left pectoral region after treatment for dental caries. The patient was a product of a normal full-term pregnancy of a healthy Korean couple. Birth weight was 2.98 kg, and no perinatal problems were encountered. Motor and cognitive development was within the normal range. Subcutaneous migrating nodules were noted over the scalp at age 2 and over the posterior neck at age 4. Flare-ups and stiffness of the neck and back developed starting at age 6, and then progressed to the extremities. Physical examination revealed a completely stiff neck, back, and right shoulder. The upper left and lower right extremities maintained a functional range of joint motion. The feet and toes appeared normal.

Figure 1A:
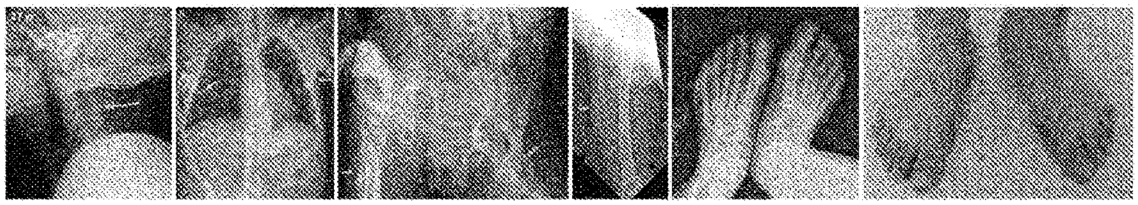

At age 22, the patient's height was 145 cm ($z<-4$) and weight was 57 kg. The whole neck and back, both shoulders and hips, and the left knee were completely fixed. Both elbows maintained only 10 to 30 degrees of flexion-extension motion, and the right knee maintained 80 degrees of motion. Radiographic examination showed heterotopic ossifications in the back muscles, periscapular muscles, peripelvic and thigh muscles (see FIG. 1*a*). Ankylosis of the posterior column of upper cervical vertebrae was also noted. It was noteworthy that there was no anomaly in the toes (see FIG. 1*a*). The patient recovered uneventfully from laparotomy for pyloric stenosis in childhood. At age 19, he developed severe dizziness. Brain MRI revealed multifocal gadolinium-enhanced tumors involving the suprasellar area, septum pellucidum, and medulla oblongata. They were clinico-radiologically diagnosed as mixed germ cell tumors because the serum beta-hCG level was moderately elevated. After radiation therapy, the tumors disappeared, and the patient has remained in complete remission for 3 years, with diabetes insipidus as its sequelae.

Methods

Genomic DNA was obtained from the proband, the sibling and his parents, and dermal fibroblast cells were derived from the proband, after obtaining written informed consent. The institutional Review Board of the Seoul National University Hospital, Seoul, South Korea, approved this study.

(1) Cell Culture, DNA Construction, Mutagenesis and FOP Cell Line Establishment

Patient-derived dermal fibroblasts and BJ (Normal) cells were grown in high-glucose and no-glutamine DMEM (GIBCO, Cat #10313) supplemented with 15% fetal bovine serum (FBS, GIBCO), Glutamax™ (GIBCO, Cat #35050-061) and non-essential amino acid (GIBCO, Cat #11140-050) and penicillin and streptomycin (GIBCO, 15140-122). Fibroblasts were incubated in 5% $CO_2$ and 3% $O_2$ at 37° C. BJ foreskin fibroblasts were obtained from ATCC. HEK293T, HeLa and U20S cells were grown in high-glucose DMEM (GIBCO, Cat #11965) supplemented with 10% FBS (GIBCO) and 1× penicillin and streptomycin (GIBCO, Cat #15140-122) and they were incubated in 5% $CO_2$ at 37° C. C2C12 myoblasts were cultured in high-glucose, glutamine and sodium pyruvate DMEM (GIBCO, Cat #11995) supplemented with 15% FBS and 1× penicillin and streptomycin at 37° C. in 5% $CO_2$ humidified atmosphere. Undifferentiated C2C12 cells were sparsely maintained in a polystyrene cell culture dish to prevent myogenesis induced by cell contact. C3H10T1/2 fibroblasts were cultured in high-glucose, glutamine and sodium pyruvate DMEM (GIBCO, Cat #11995) supplemented with 10% FBS and 1× penicillin and streptomycin and they were incubated in 5% $CO_2$ at 37° C. Primary patient-derived fibroblasts and BJ cells were immortalized by expressing the catalytic subunit of human telomerase (hTERT) through lentiviral transduction and transformed by the human papilloma virus E6 and E7 protein through retroviral transduction. BMPR2 cDNA was obtained from addgene. BMPR2 cDNA was cloned to EcoRI restriction sites in pcDNA6/V5-HisABC vector using In-Fusion HD Cloning kits (Takara, Cat #638920) and pDONR223 BP vector and later pHAGE-HA-FLAG LR vector using Gateway cloning system (Thermo Fisher Scientific). C.1126G>A BMPR2 mutation was generated by QuikChange II XL Site-Directed Mutagenesis Kit (Agilent Genomics) with the following primer; BMPR2-F (SEQ ID No. 1) 5'-GGGGACAAGTTTGTACAAAAAAGCAGGCTTAATGACTTCCTCGCTGCAGCGGC-3', BMPR2-R (SEQ ID No. 2) 5'-GGGGACCACTTTGTACAAGAAAGCTGGGTCTCACAGACAGTTCATTCC-3'. Cell lines stably expressing BMPR2 or BMPR2 mutants were generated by lentiviral transduction as previously described (see non-patent document 26).

(2) Osteogenic Differentiation

BJ and patient-derived dermal fibroblasts ($8\times10^4$ cells/well) were seeded into 24-well cell culture plates and then cultured in DMEM (GIBCO, Cat #10313) supplemented with 15% FBS, 1% Glutamax, 1% non-essential amino acid and 1% penicillin-streptomycin at 37° C. with 5% $CO_2$ and 3% $O_2$. To induce differentiation, growth medium was replaced into DMEM supplemented with 2% horse serum (GIBCO, Cat #16050) after cells reached 80~90% confluence. Cells were maintained without or with recombinant human BMP2 or BMP4 (R&D SYSTEMS) and replaced with fresh medium every 2~3 days for 2~21 days. C2C12 cells were seeded into 24-well cell culture plates at a density of $4\times10^4$ cells/well. Cells were grown in DMEM (GIBCO, Cat #11995) supplemented with 15% FBS at 37° C. with 5% C02. Cells with 80~90% confluence were replaced by osteogenic differentiation DMEM (GIBCO, Cat #11995) containing 100 nM dexamethasone, 10 mM R-glycerophosphate, and 50 μM ascorbic acid-2-phosphate (all from Sigma) supplemented with 2% horse serum. C2C12 were treated with BMP2, BMP4, dorsomorphin (Sigma), or SB431542 (Sigma) and maintained with replacement of fresh medium every 2~3 days for 3~21 days.

(3) Chondrogenic Differentiation

For chondrogenesis, C3H10T1/2 cells were cultured by micromass technique, high density dot culture. First, cells were resuspended in DMEM supplemented with 10% FBS and 1× penicillin-streptomycin at a concentration of $10^7$ cells/ml and a 10 μl droplet of the cell suspension was placed in the center of a well of 12-well cell culture plates followed by incubation at 37° C. and 5% $CO_2$. After 2 hours, 1 ml chondrogenic differentiation medium consisting of 1% FBS, 1% Insulin-Transferrin-Selenium (GIBCO), 0.1 μM dexamethasone, 0.17 mM ascorbic acid-2-phosphate, 0.35 mM proline (Sigma), and 0.15% glucose (Sigma) was added in each well and cells were maintained without or with human recombinant BMP2.

(4) Whole Exome Sequencing and DNA Analysis

Written informed consent was obtained from the affected individual. The Institutional Review Board of the Seoul National University Hospital, Seoul, South Korea approved the studies. Genomic DNAs were extracted from whole blood and sequencing libraries were prepared using Twist modular library preparation kits. SureSelect Human All Exon V5 baits (Agilent, Santa Clara, CA) covering all exon regions were used. Targeted sequencing was performed with 101 base pair (bp) paired-end reads on an Illumina HiSeq2500 platform (Illumina, San Diego, CA). Sequenced reads were aligned to human genome reference sequence (hg19) using Burrows-Wheeler Aligner (BWA) version 0.7.5a with the Maximum Entropy Method (MEM) algorithm. At the same time, the aligned reads were selected mapping phred quality score above 30, converted to binary alignment map (BAM) format and sorted ordering by genomic position using SAMTOOLS version 1.2. For high performance accurate variant calling, i) PCR duplicates reads were marked using MarkDuplicates of Picard tools version 1.127 (http://broadinstitute.github.io/picard/). ii) Insertion and deletion (Indel) realignment were performed with known Indels from Mills and 100G gold standard using RealignerTargetCreator and IndelRealigner of Genome Analysis Tool Kit (GATK) version 3.1-1. iii) Base quality score was recalibrated using machine learning model with known single nucleotide polymorphisms (SNPs) and Indels from dbSNP138, Mills and 1000 Genome Project phase I by BaseRecalibrator and PrinReads of GATK. Manipulated BAMs were simultaneously called and genotyped of single nucleotide variants (SNVs) and Indels by GATK UnifiedGenotyper uses a Bayesian genotype likelihood model. Variants were recalibrated with reference variants such as dbSNP138, Mills Indels, HapMap and Omni using GATK VariantRecalibrator and ApplyRecalibration. Variants were annotated various information using ANNOVAR described below: i) population database such as 1000 genome phase III, ExAC and KRGDB (http://coda.nih.go.kr/coda/KRGDB/), ii) disease database such as OMIM, sequencing database such as RefSeqGene, iii) in silico predictive algorithms such as FATHMM, MutationAssessor, MutationTaster, SIFT, Polyphen, GERP and Phylop for interpretation and classification of variants following ACMG guideline. Classified pathogenic or likely pathogenic variants were confirmed by Sanger sequencing. Copy number variants (CNVs) were calculated using aligned read counts in target region by in-house relative comparison method. Detected and classified pathogenic CNVs were re-confirmed by array comparative genomic hybridization (array CGH) (see non-patent documents 27 to 31).

(5) CRISPR-Cas9 Mediated Gene Correction

Along with 10 μM single-stranded oligodeoxynucleotides (ssODN) donor template, 4 μg of *S.pyogenes* Cas9 (SpCas9) protein and 1 μg of guide RNA selectively targeting mutated allele of FOP patients were prepared as RNP complex and delivered into fibroblasts obtained from patients with Neon electroporator (Invitrogen). Target sequence (SEQ ID No. 3) for CRISPR-Cas9 is as follows; 5'-agataatgcagccataagcaagg-3' (PAM sequence:underlined). To distinguish the corrected allele from wild type and to prevent the recurrent cleavage, donor template (SEQ ID No. 4) was designed as follows; 5'-ccatgaggctgactggaaatagactggtgcgcccaggggaggaagataatgcagccatCTCcga ggtgagtgtatacaaaaggtatcacactgatgtactttgaaatgataatttaatta (upper underlined: codon matched sense mutation, italic underlined: corrected base). 1 week after electroporation, frequency of properly corrected allele from pooled fibroblasts were analyzed by targeted deep sequencing. Based on that frequency, cells were dissociated and re-plated in 96-well plates at the density of ⅓ cell per well to obtain single cell colony. After single cell colony isolation, gDNAs of each clone were harvested and analyzed by targeted deep sequencing, and proper colonies were selected for further experiments.

(6) Targeted Deep Sequencing

To quantify Indel ratio and analyze the sequence after CRISPR-Cas9 treatments, target region was amplified with PCR primers hybridizing the target amplicon sequences with illumina barcode sequences by nested PCR. PCR products were purified, denatured by NaOH, and subjected to 2×250 paired-end sequencing with an Illumina MiSeq. Paired-end reads from MiSeq were analyzed by Cas-Analyzer (http://www.rgenome.com). PCR primers used in this experiment were as follows; hBMPR2 E7 F1 (SEQ ID No. 5): 5'-gcctccttttacagccctat-3', hBMPR2 E7 R1 (SEQ ID No. 6) 5'-aactttacccttgcctcaaa-3', hBMPR2 E7 dF1 (SEQ ID No. 7) 5'-ACACTCTTTCCCTACACGACGCTCTTCCGATCTacagcagaaatgtcctag, hBMPR2 E7 dR1 (SEQ ID No. 8) 5'-GTGACTGGAGTTCAGACGTGTGCTCTTCCGATCTctctttaccttaggtgat.

(7) Small Interfering RNA, siRNA siRNAs were transfected twice into cells, first by reverse transfection and 24 hours later by forward transfection using Lipofectamine RNAiMAX reagent (Invitrogen) as suggested by the manufacturer's instructions. ACVR1 (ID #s974, s976), TGFBR1 (ID #s14071, s14073), and BMPR2 (ID #s2044, s2045, s2046) siRNAs were purchased from Thermo Fisher Scientific. Pools of two or three siRNAs were used with a final siRNA concentration of 25 nM.

(8) Luciferase Reporter Assay 293T cells were plated in the Falcon® 96-well white flat bottom tissue culture-treated microtest assay microplate (CORNING) In each well, 5,000 cells were plated in 100 μl 10% DMEM media. 24 hours after plating, cells were transfected with pcDNA-empty vector, pcDNA6/V5-HisA-wildtype BMPR2 or -mutant BMPR2, pGL3-BMP responsive elements-luciferase (hereafter pGL3-BRE-luc, offered from addgene plasmid #45126), and pNL1.1.TK internal control vector for the assay, using calcium phosphate transfection Kit (Invitrogen). The amounts of WT or mutant BMPR2, and pGL3-BRE-luc, and pNL1.1 from Nano-Glo® Dual-Luciferase® Reporter Assay Kit (Promega) were determined according to a protocol of calcium phosphate transfection from Clontech Laboratories; 50ng of WT BMPR2 or mutant BMPR2 and pGL3-BRE-luc and 5ng of pNL1.1.TK were used and then 2M Calcium Solution and sterile water were added in each DNA tube. The same volume of 2×HEPES-Buffered Saline (HBS) was added to Calcium-DNA mixture dropwise and incubated at room temperature. After 15 minutes, the transfection solution was carefully added to culture plate medium and maintained at 37° C. in a $CO_2$ incubator. The next day, the calcium phosphate-containing medium was removed from cells and replaced with fresh complete growth medium. A volume of One-Glo™ EX Luciferase assay Reagent was equally added to the culture medium volume to each well and placed on an orbital shaker at 300 rpm for 3 minutes. Luminescence was measured as integration times of 1 second by GloMax® Discover System (Promega). For measurement of NanoLuc® luciferase activity, a volume of NanoDLR™ Stop & Glo® Reagent was equally added to the original culture medium volume to each well and then luminescence was analyzed. The BRE reporter luminescence was normalized to NanoLuc® luciferase activity.

(9) Western Blotting and Immunoprecipitation

Cells were plated either in 60 mm or 100 mm plate with 70% confluency. The next day, plasmid DNA was transfected into HEK293T cells by Lipofectamine 2000. After 4 hours, cells were changed into serum free medium and treated with human recombinant activin A (R&D SYSTEMS) the next day. Cells were harvested and lysed by lysis buffer (50 mM Tris-HCl pH7.5, 150 mM NaCl, and 0.5% Nonidet P-40) containing a protease inhibitor cocktail (Roche) and quantified by Protein Assay Dye Reagent Concentrate (Bio-Rad) and NanoDrop (Thermo Fisher Scientific). Proteins were separated by 8~15% sodium dodecyl sulfate-polyacrylamide gel electrophoresis (SDS-PAGE) and gels were blotted onto polyvinylidene difluoride (PVDF) transfer membrane with 0.45 μm pore size (Merck Millipore). Blots were blocked in 1×PBS with 0.1% Tween-20 (Sigma) containing 5% Difco™ Skim Milk (BD) for 1 hour at room temperature and incubated with anti-VS-Tag (Invitrogen, #R960-25), anti-phospho-SMAD1/5/9 (Cell Signaling Technology, #13820), anti-SMAD1 (CST, #6944), anti-SMAD5 (CST, #12534), anti-phospho-SMAD2 (CST, #3108), anti-SMAD2 (CST, #5339), anti-SMAD4 (CST, #9515), anti-ID1 (SANTA CRUZ BIOTECHNOLOGY, sc-488), anti-ID3 (SCBT, sc-490), anti-HA (Covance, MMS-101R), anti-SOX9 (CST, #82630), anti-BMPR2 (CST, #6979), anti-Osteocalcin (Merck Millipore, AB10911), anti-Alkaline Phosphatase (abcam, ab108337), anti-RUNX2 (SCBT, sc-10758) and anti-GAPDH (SCBT, sc-25778) as a loading control at 4° C. for overnight. After blots were washed four times in 1×PBST for 1 hour at room temperature, anti-mouse secondary (Jackson ImmunoResearch, 115-035-003) or anti-rabbit secondary (Jackson ImmunoResearch, 111-035-003) was used at 1:2500 for 2 hours at room temperature and then bands were detected by enhanced chemiluminescence solution (Bio-Rad) using ChemiDoc System (Bio-Rad). The band image was analyzed with Image Lab™ Software (Version 5.2.1, Bio-Rad).

For immunoprecipitation, transiently transfected HEK293T cells were lysed and sonicated in lysis buffer at 4° C. Crude lysates cleared by centrifugation at 15,000 rpm at 4° C. for 20 minutes. Supernatants were incubated with Monoclonal Anti-HA-Agarose antibody (Sigma) for 2 hours at 4° C. Immunocomplex was washed five times with lysis buffer and then SDS-PAGE and western blotting were performed.

(10) Real-Time Quantitative Reverse Transcription PCR

Total RNA of the cells was extracted using RNeasy Mini Kit and QIAshredder (QIAGEN) and quantified using NanoDrop instrument. 1 μg of total RNA was used to cDNA synthesis using a SuperScript III First-Strand Synthesis System (Invitrogen). Gene expression was quantified by 2× qPCRBIO SyGreen Blue Mix Lo-R0X (PCRBIOSYSTEMS) performed on LightCycler® 96 (Roche). Quantification cycle (Cq) values of samples were analyzed by LightCycler® 96 Application Software (Version 1.1). Gene-specific primers are shown in Table 1 below.

TABLE 1

| sample | | Sequence 5'→3' | Notes |
|---|---|---|---|
| mCol2a1 | sense | CCTCCGTCTACTGTCCACTGA | SEQ ID No. 9 |
| | antisense | ATTGGAGCCCTGGATGAGCA | SEQ ID No. 10 |
| mCol10a1 | sense | AACAGGTATGCCCGTGTCTG | SEQ ID No. 11 |
| | antisense | TCATCAAATGGGATGGGGGC | SEQ ID No. 12 |
| mAggrecan | sense | TGGCTTCTGGAGACAGGACT | SEQ ID No. 13 |
| | antisense | TTCTGCTGTCTGGGTCTCCT | SEQ ID No. 14 |
| mGapdh | sense | CATGTTCCAGTATGACTCCACTC | SEQ ID No. 15 |
| | antisense | GGCCTCACCCCATTTGATGT | SEQ ID No. 16 |
| hPAI-1 | sense | TCCTGGTTCTGCCCAAGTT | SEQ ID No. 17 |
| | antisense | CCAGGTTCTCTAGGGGCTTC | SEQ ID No. 18 |
| hPDGFB | sense | CTGGCATGCAAGTGTGAGAC | SEQ ID No. 19 |
| | antisense | CGAATGGTCACCCGAGTTT | SEQ ID No. 20 |

TABLE 1-continued

| | sample | Sequence 5'→3' | Notes |
|---|---|---|---|
| hTHBS-1 | sense | CAATGCCACAGTTCCTGATG | SEQ ID No. 21 |
| | antisense | TGGAGACCAGCCATCGTC | SEQ ID No. 22 |
| hGAPDH | sense | AGCCACATCGCTCAGACAC | SEQ ID No. 23 |
| | antisense | GCCCAATACGACCAAATCC | SEQ ID No. 24 |

(11) Alizarin S Staining (Mineralization Assay)

The mineralization was determined by staining with Alizarin Red S at 21 days after osteogenic differentiation. For preparation of solution, 2 g Alizarin Red S (Sigma) was dissolved in 100 ml distilled water and then adjusted to pH4.3 with HCl or $NH_4POH$. Differentiated cells were carefully washed with PBS and fixed with 4% paraformaldehyde (Sigma). After 30 minutes carefully washed the cells with distilled water followed by prepared stain solution was enough added to the cells for 45 minutes at room temperature in the dark. The cells were washed four times with distilled water and carefully aspirated. The differentiated cells are stained darker red with calcium deposits. After photography using digital camera (Nikon), the stained cells were lysed with 10% cetylpyridinium chloride (sigma) dissolved in 10 mM sodium phosphate buffer (1 M $NaH_2PO_4$ monobasic and 1 M $Na_2HPO_4$ dibasic, pH7.0) and then quantified at 560 nm using a GloMax® Discover System.

(12) Alkaline Phosphatase (ALP) Staining and Activity

For detection of alkaline phosphatase, cells were firstly cultured with osteogenic differentiation media for 2 or 3 days. Cells were cautiously washed with PBS and then fixed with 4% paraformaldehyde. After 1 minute, cells were rinsed with Washing Buffer (0.05% Tween 20 in PBS), subsequently treated with substrate solution which was dissolved one BCIP/NBT tablet (Sigma) in 10 ml distilled water. For staining, the cells were incubated at room temperature in the dark for 10 minutes monitoring staining progress every 2~3 minutes. Carefully aspirated the substrate solution and rinsed the cell with Washing Buffer. The higher alkaline phosphatase, the more intense the dark blue-violet. For ALP activity, cultured cells were washed with PBS and lysed with cold alkaline phosphatase reaction buffer (1 M Diethanolamine and 0.5 mM Magnesium Chloride, pH9.8, Sigma). Lysates were incubated in 0.67 M p-Nitrophenyl Phosphate (pNPP) solution (Sigma) for 30 minutes at 37° C. continuing the reaction was immediately followed by monitoring in absorbance at 405 nm. Total protein was measured by using a Micro-BCA protein assay kit (Thermo Fisher Scientific) and read at 560 nm using a GloMax® instrument. The enzymatic ALP activity was normalized to the protein content of the samples.

(13) Alcian Blue Staining

To visualize ability of chondrogenesis, stain solution (pH1.0) was prepared with 1 g Alcian blue 8GX (Sigma) in 100 ml 0.1 M HCl. Cells were fixed with 4% paraformaldehyde in PBS for 20 minutes at room temperature and then rinsed 3 times with PBS. Alcian blue solution was used to stain the cells at room temperature in the dark. Next day, cells were washed once with 0.1 M HCl and twice with PBS. After taking a picture, the dye was extracted by Guanidine-HCl (Sigma) for 2 hours at room temperature and then read in absorbance at 600 nm using a GloMax® instrument.

Figure 1B:
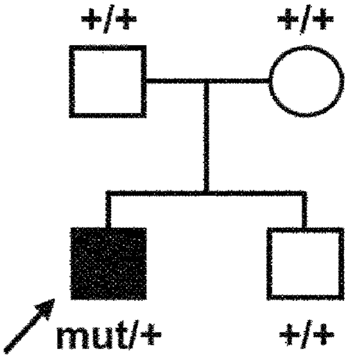

Experimental Result 1: Verification of Applicability of BMPR2-E376K Mutant to Treatment of Bone Diseases The clinical manifestations were consistent with FOP, except for the absence of a big toe anomaly (see FIG. 1*a*). Full sequencing of the coding region of ACVR1 (MIM #102576) of the proband showed only two silent sequence variations, both of which were previously reported in normal population: c.270C>T (NCBI dbSNP rs2227861) and c.690G>A (rs1146031). Then, whole exome sequencing was performed on the genomic DNA from the proband and a heterozygous variation in BMPR2 (MIM #600799), c.1126G>A (p.E376K) was identified. Sanger sequencing and restriction enzyme digestion confirmed the sequence variation in the proband and absence in the genome of the parents and the sibling (see FIGS. 1*b* to 1*c*). The BMPR2-E376K mutation is located in the kinase domain (see FIG. 1*d*) (see non-patent document 13) where the sequence is highly conserved among species (see FIG. 1*e*). The BMPR2 sequence variation was not found in the general populations of the 100 genome, ExAC, dbSNP, or Exome Sequencing Project databases.

To gain insight into the molecular basis of the disease phenotype, BMPR2 protein changes were determined by immunoblotting the lysates prepared from dermal fibroblasts obtained from the patient's skin and a normal control. As shown in FIG. if, lysates from the patient-derived cells showed constitutive phosphorylation of SMAD1/5/9, and the resultant increased expression of ID1 and ID3, which was not the case in the lysates prepared from the normal BJ control cells (see FIG. if). Interestingly, it was noticed that SMAD2 was also phosphorylated in these cells. In addition, patient-derived cells cultured in the differentiation media expressed a group of proteins (see non-patent document 14) implicated in bone development including osteocalcin (OCN), alkaline phosphatase (ALP), and RUNX2, even in the absence of BMP treatment (see FIG. if, right panel). These molecular changes were reflected at the cellular level. ALP expression is known as a molecular marker for bone development (see non-patent document 15). As expected, the patient-derived cells were positive for ALP staining and ALP activity while normal control cells barely express the ALP (see FIG. 1*g*). Furthermore, it was found that calcium was accumulated in the culture of the patient-derived cells, which was determined by alizarin red S staining after 21 days in culture (see FIG. 1*h*) (see non-patent document 16). Taken together, these findings strongly suggest that the BMPR2-E376K variant constitutively activates BMP signaling, even in the absence of BMP treatment.

Functional validation of pathogenicity of the potential causative mutation is critical. DNA sequence analysis suggested the BMPR2-E376K variant was functionally dominant, and therefore it was hypothesized that if the mutated BMPR2 allele was deleted, the hyperactivated BMP signaling would return to normal. To this end, the mutated BMPR2 allele was first deleted using CRISPR-Cas9 in the patient-derived cells. At the same time, the c.1126G>A variant was reverted back to the WT sequence using CRISPR-Cas9 knock-in methods. A large number of single clones were carefully isolated and sequences of the BMPR2 gene in individual clones were determined using a MiSeq system (see FIG. 2*a* and FIG. 4). It was found that both knock-out and knock-in clones lost the SMAD1/5/9 phosphorylation (see FIG. 2*b*), ALP staining, and calcium deposition (see FIG. 5), demonstrating that the BMPR2-E376K variant is causative for the constitutive BMP activation and resultant outcomes.

Next, the inventors reasoned that ectopic expression of the BMPR2-E376K variant in different cell types would recapitulate the molecular and cellular changes caused by expression of the functionally dominant genomic variant. To test this, an empty vector, WT BMPR2, or BMPR2-E376K were expressed in HEK293T cells, respectively (see FIG. 2*c*) and it was found that only the expression of BMPR2-E376K led to hyperphosphorylation of SMAD1/5/9 and expression of ID1 and ID3. In addition, to test if enhanced BMP signaling due to the expression of BMPR2-E376K results in BMP response gene expression, a transcriptional reporter assay system in which luciferase expression is controlled by BMP-responsive elements was established (see non-patent document 7). As expected, it was noticed that expression of BMPR2-E376K in HEK293T cells led to significant enhancement of luciferase activity (see FIG. 2*d*). In the same experimental setting, similar results were obtained when the known causative ACVR1-R206H mutant was expressed in HEK293T cells (see FIGS. 2*c* to 2*d*, right panels). Taken together, these findings demonstrate the dominant gain-of-function features of the BMPR2-E376K mutation.

Figure 2A:
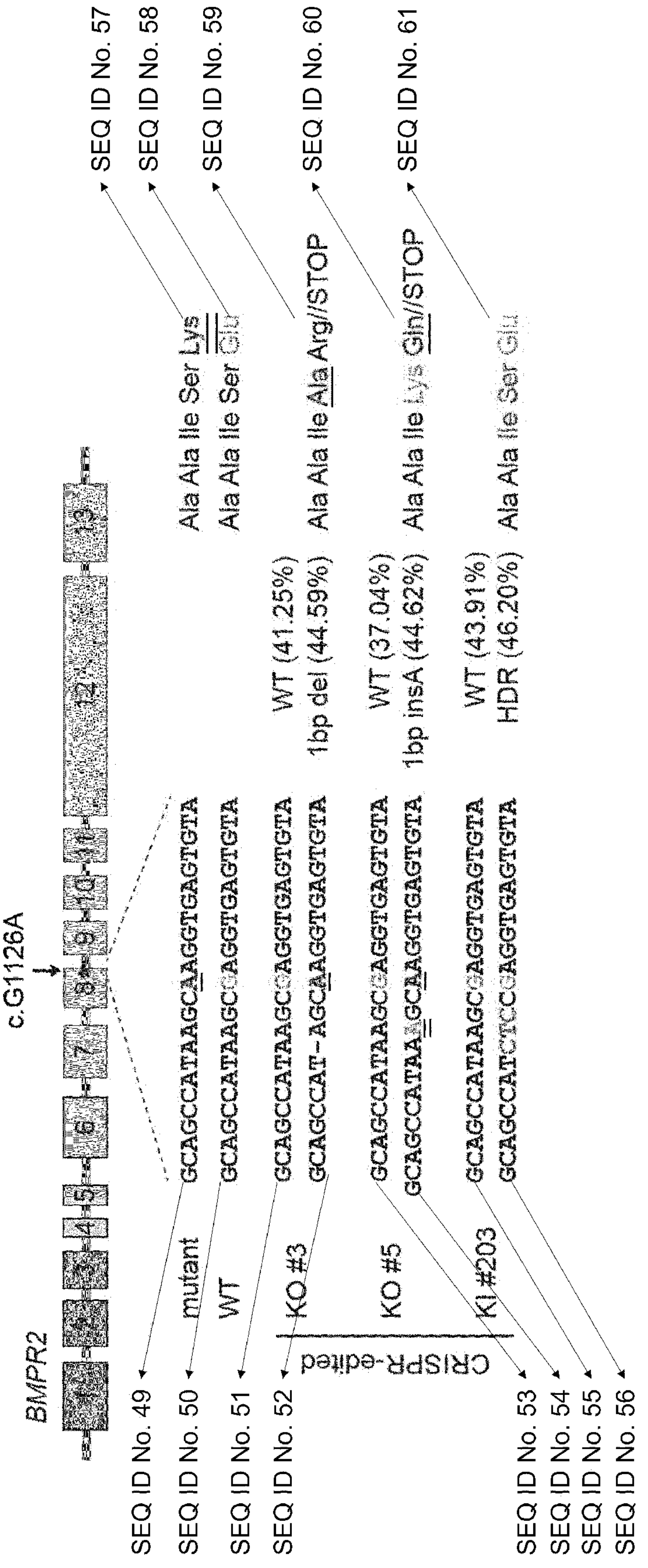
FIGS. 2*a* to 2*g* are photos and graphs related to the functional validation of pathogenicity of the BMPR2-E376K variant.
Figure 2B:
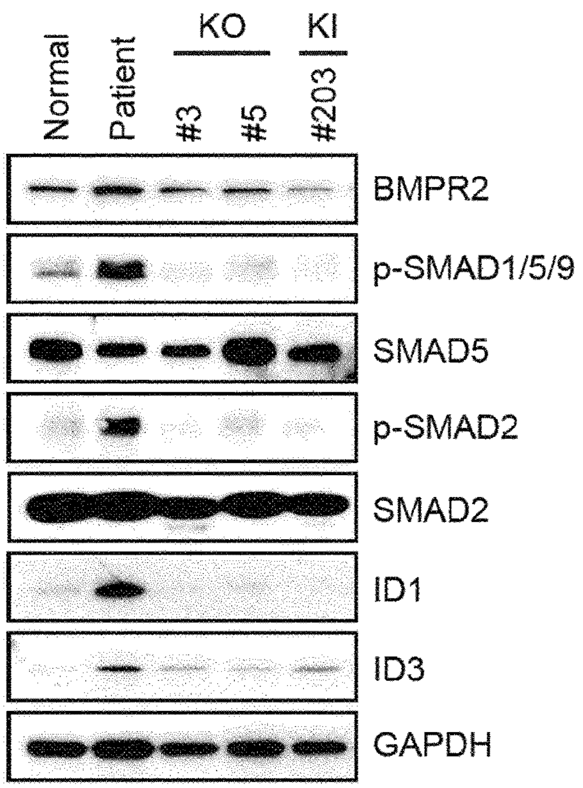
Figure 2C:
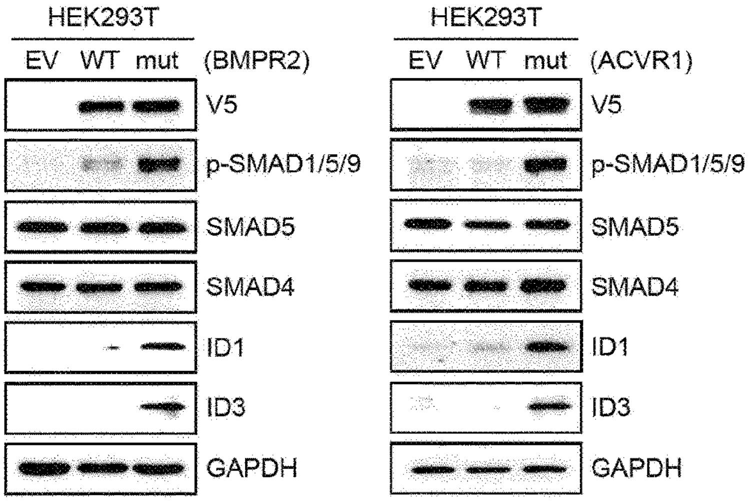
Figure 2D:
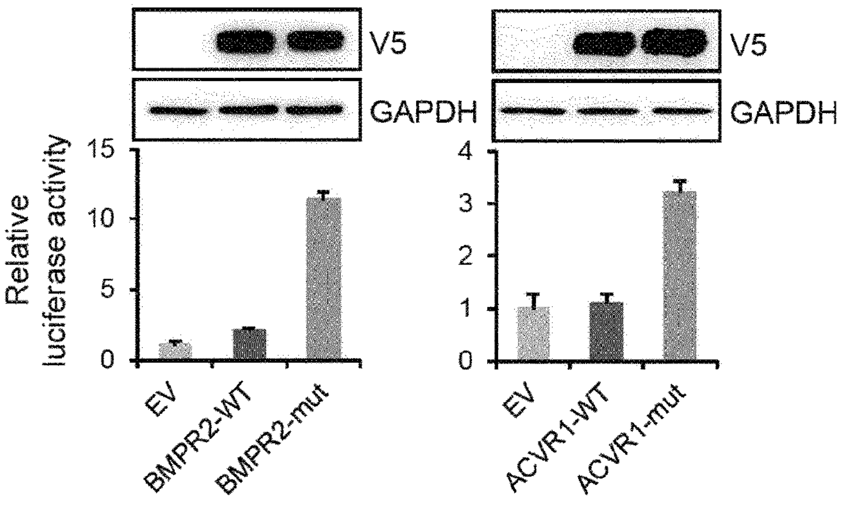
Figure 2E:
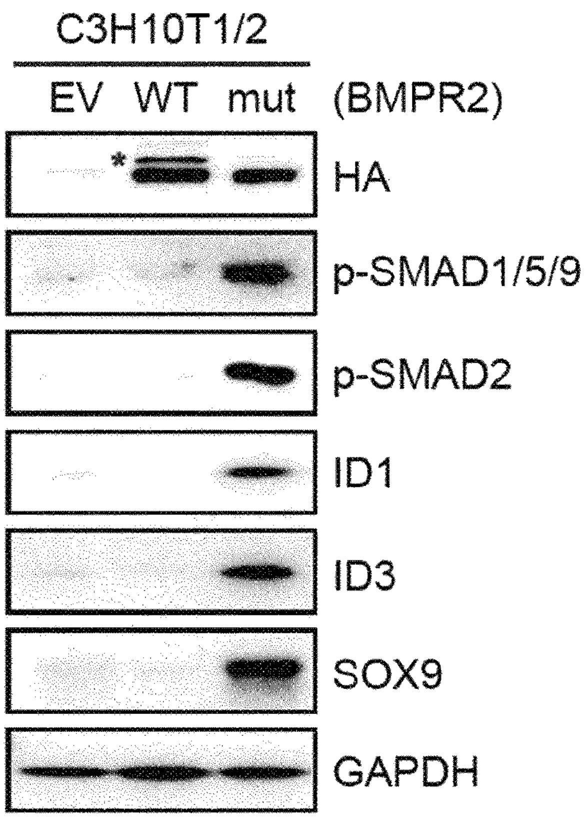
Figure 2F:
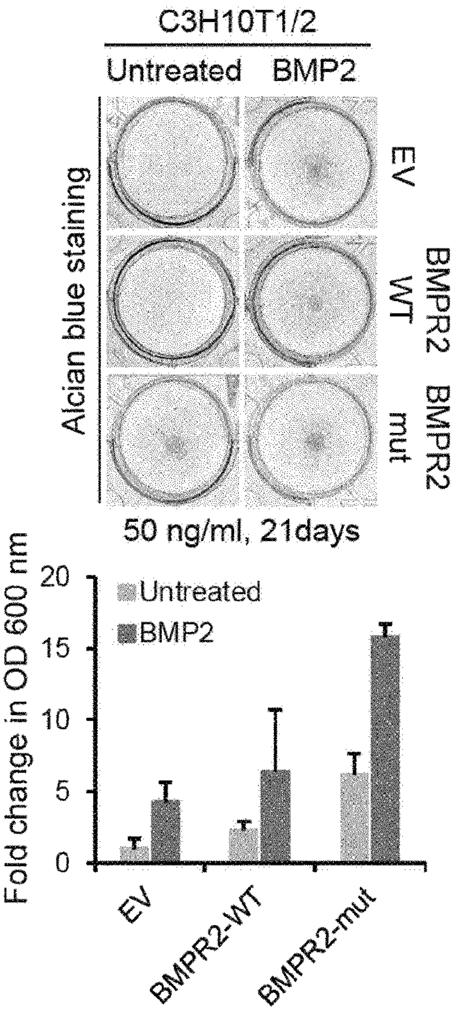
Figure 2G:
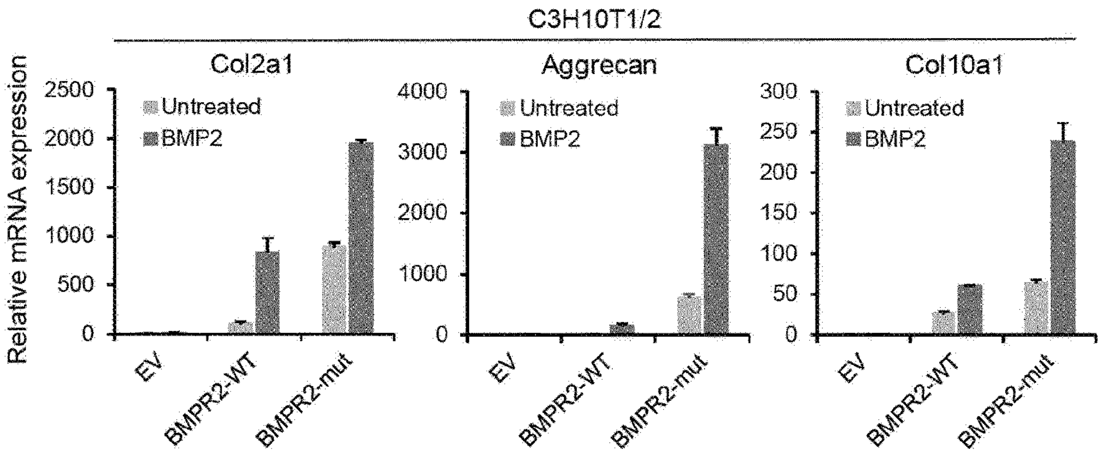

Endochondral heterotopic ossification in FOP lesions involves chondrogenic differentiation from mesenchymal stem cells (MSCs) due to the enhanced BMP signaling, which later turns into mature bone tissue (see non-patent document 14). As the BMPR2-E376K mutant stimulates BMP signals in the absence of BMP ligands, the inventors hypothesized that the BMPR2-E376K variant might force the MSCs to become chondrocytes. To test this idea, an empty vector, WT BMPR2, or BMPR2-E376K were individually expressed in mouse MSC cell line C3H10T1/2. As shown in FIG. 2*e*, it was found that temporal expression of BMPR2-E376K led to phosphorylation of SMAD1/5/9 and expression of its downstream effectors including ID1, ID3, and SOX9. In addition, it was found that C3H10T1/2 cells expressing BMPR2-E376K were forced to become chondrocytes, based on the Alcian blue staining (see FIG. 2*f*). Indeed, later in culture, expression of the BMPR2-E376K mutant showed enhanced expression of COL2A1, COL10A1, and Aggrecan, all of which are highly expressed in osteoblasts (see FIG. 2*g*) (see non-patent document 17). Altogether, these findings demonstrate that BMPR2-E376K is causative for the FOP phenotype and is a typical gain-of-function mutation.

BMP signaling is activated in the presence of BMP ligands, which leads to engagement of type I and type II receptors. The same is true in other cellular receptor systems, and it was reported that gain-of-function mutations in other receptors cause forced association of receptor partners, resulting in constitutive signal transduction. In an attempt to understand the molecular consequences of the gain-of-function BMPR2-E376K mutation, it was tested if the BMPR2-E376K mutant can associate with ACVR1 in the absence of BMP ligands. To this end, V5-tagged ACVR1 was transiently expressed together with either WT or mutant HA-tagged BMPR2. Surprisingly, it was found that ACVR1 co-immunoprecipitated with BMPR2-E376K, whereas WT BMPR2 did not associate with ACVR1 in the absence of BMP ligands (see FIG. 3*a*), suggestive of a molecular basis for constitutive activation of BMP signaling by the BMPR2-E376K mutant. In addition, combined expression of the ACVR1-R206H and BMPR2-E376K variants showed additive effects of SMAD1/5/9 phosphorylation (see FIG. 3*b*), indicating that BMPR2-E376K variant has a different molecular mechanism of BMP signal activation than ACVR1-R206H. However, similar to the case of ACVR1-R206H mutation (see FIG. 9) (see non-patent documents 11 and 12), it was noticed that treatment with activin A, a non-osteogenic member of the TGF-beta superfamily stimulating SMAD2/3 phosphorylation (see non-patent documents 11, 18 and 19), enhances SMAD1/5/9 phosphorylation in cells expressing BMPR2-E376K, but not empty vector or WT BMPR2 (see FIG. 3*c*). Considering the fact that activin A is an obligatory factor for the FOP phenotype, this finding further supports idea that the BMPR2-E376K mutation is causative for FOP, although the molecular mechanism remains elusive.

Figure 3A:
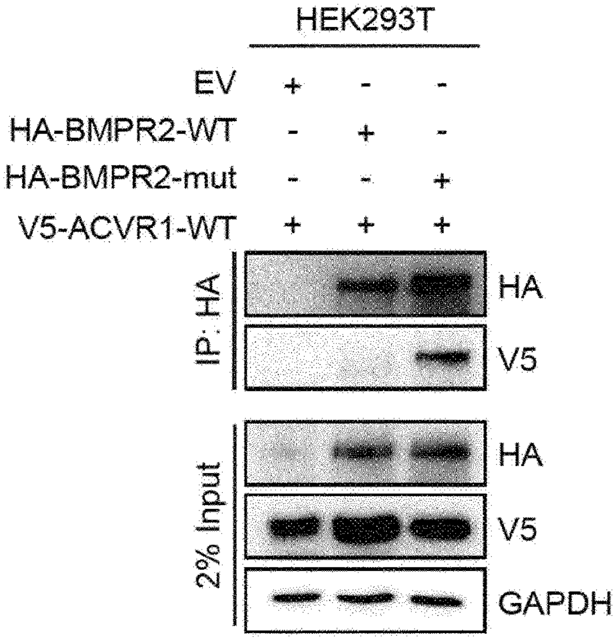
FIGS. 3*a* to 3*g* are photos related to the molecular basis of the dominant-negative functions of BMPR2-E376K.
Figure 3B:
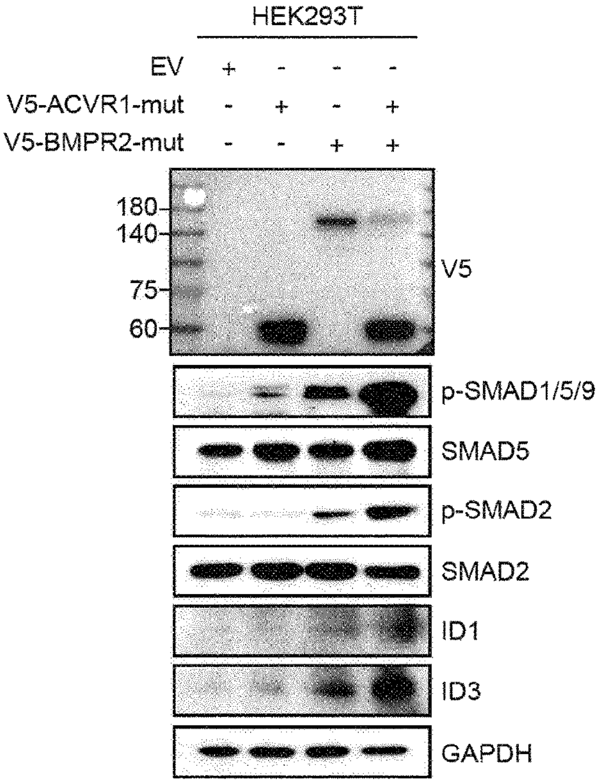
Figure 3C:
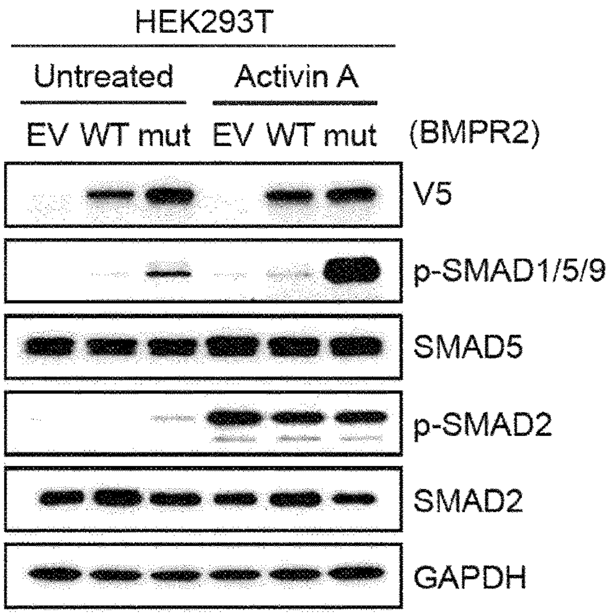
Figure 3D:
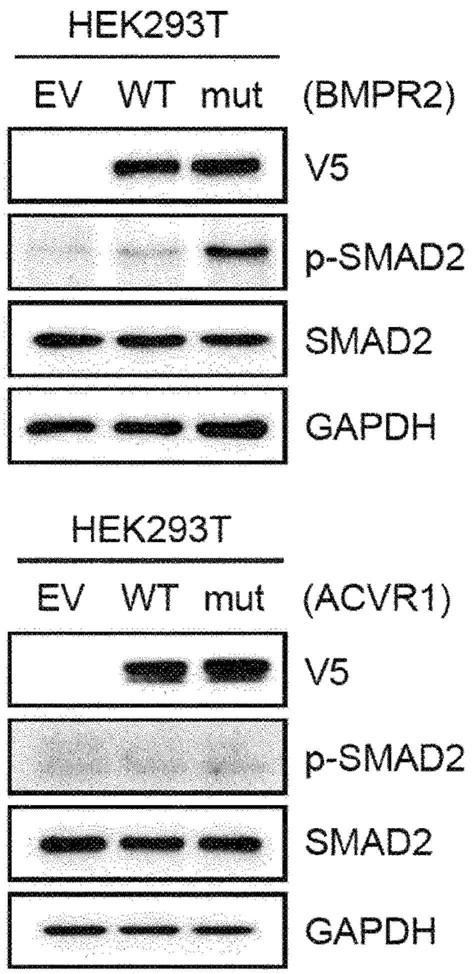
Figure 3E:
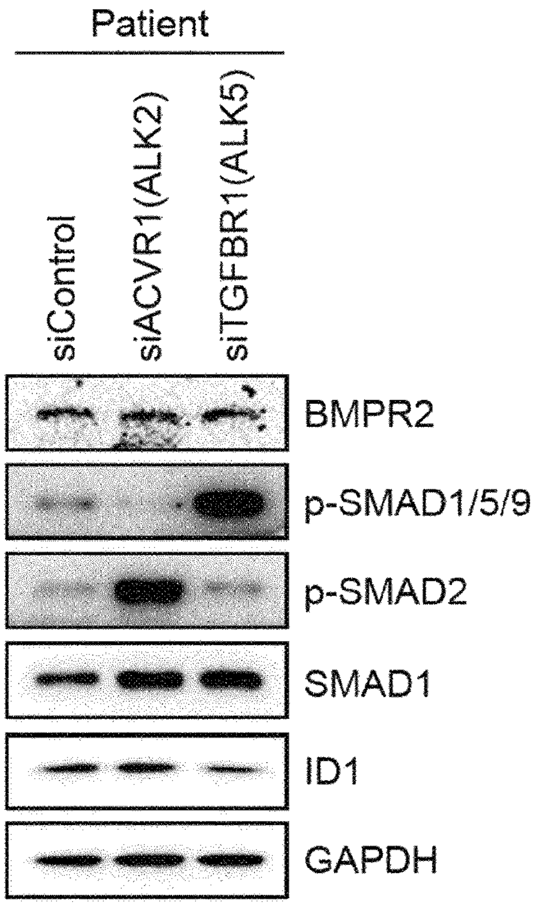
Figure 3F:
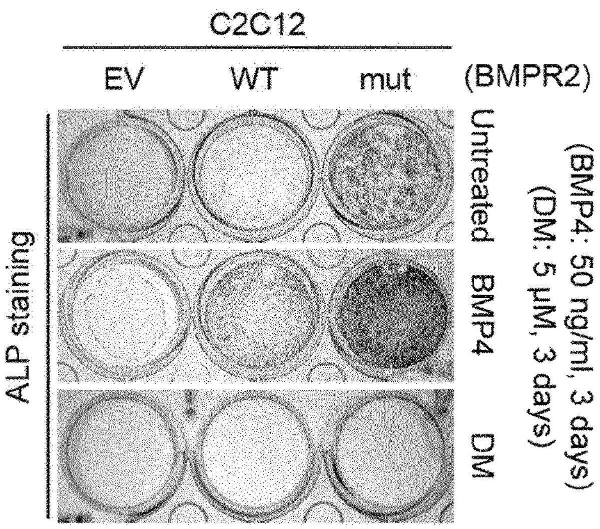
Figure 3G:
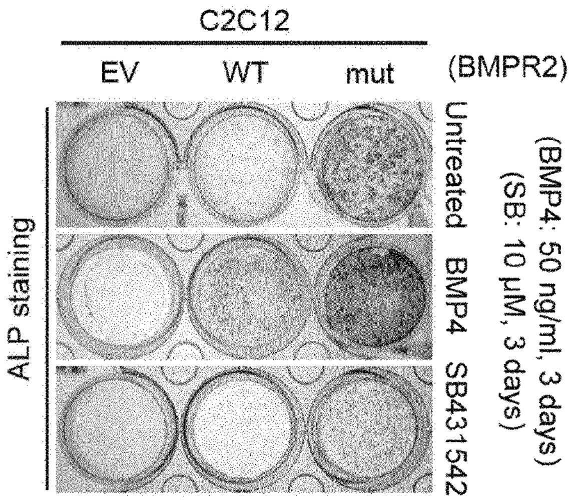
Figure 6A:
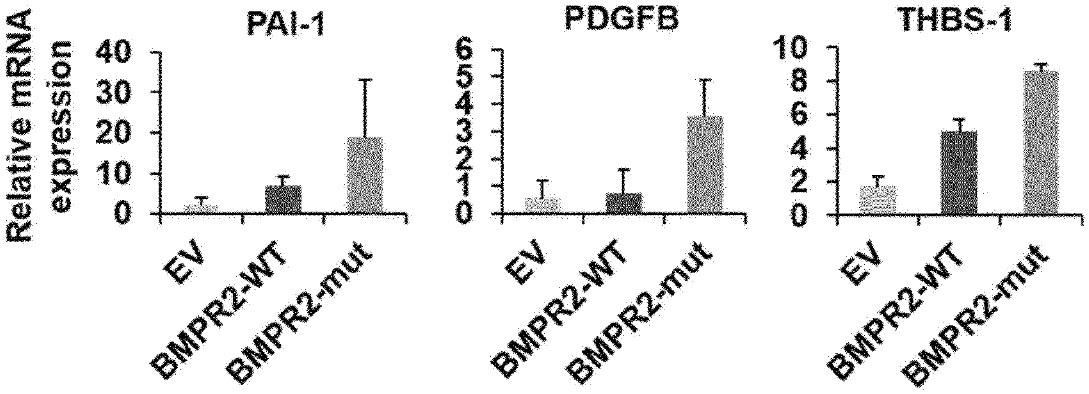
FIGS. 6*a* and 6*b* are graphs showing mRNA level of TGF-β signaling target genes. To examine mRNA expression pattern of TGFβ signaling regulated by FOP-causative variants, empty vector (EV), BMPR2-wildtype, or BMPR2 E376K (FIG. 6*a*), EV, ACVR1-wildtype, or ACVR1 R206H (FIG. 6*b*) construct was transiently transfected into HEK293T cells. Expression level of TGFβ target genes including PAI-1, PDGFB, and THBS-1 was measured by RT-qPCR.
Figure 6B:
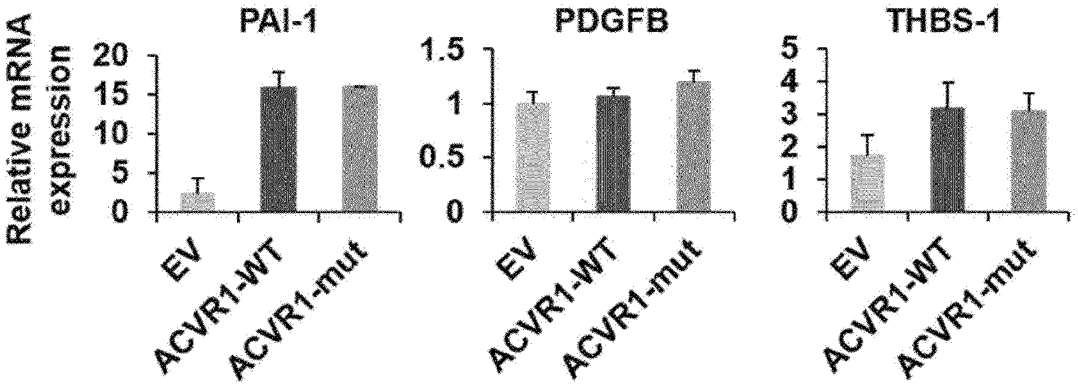
Figure 7A:
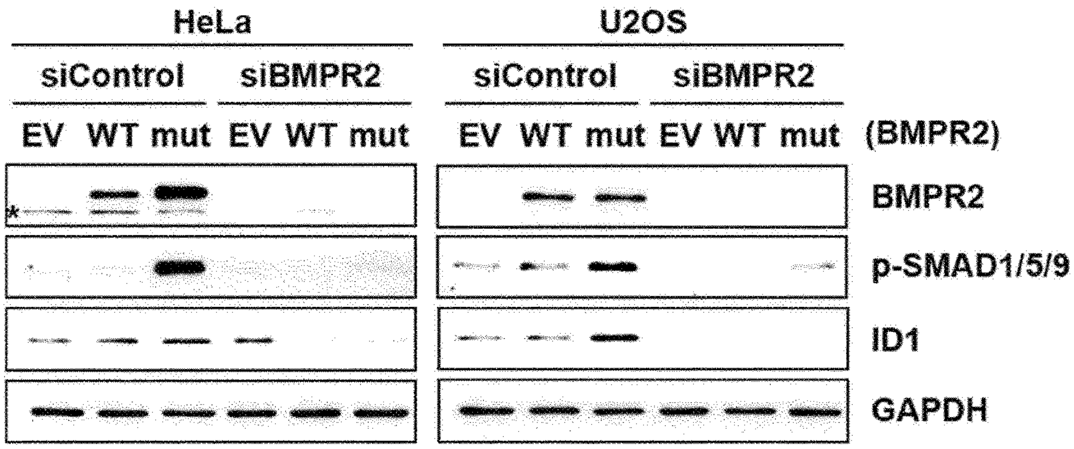
FIGS. 7*a* and 7*b* are photos showing that depletion of type I or type II TGF-β receptors by siRNA in BMPR2 E376K variant results in repression of SMAD activation.
Figure 7B:
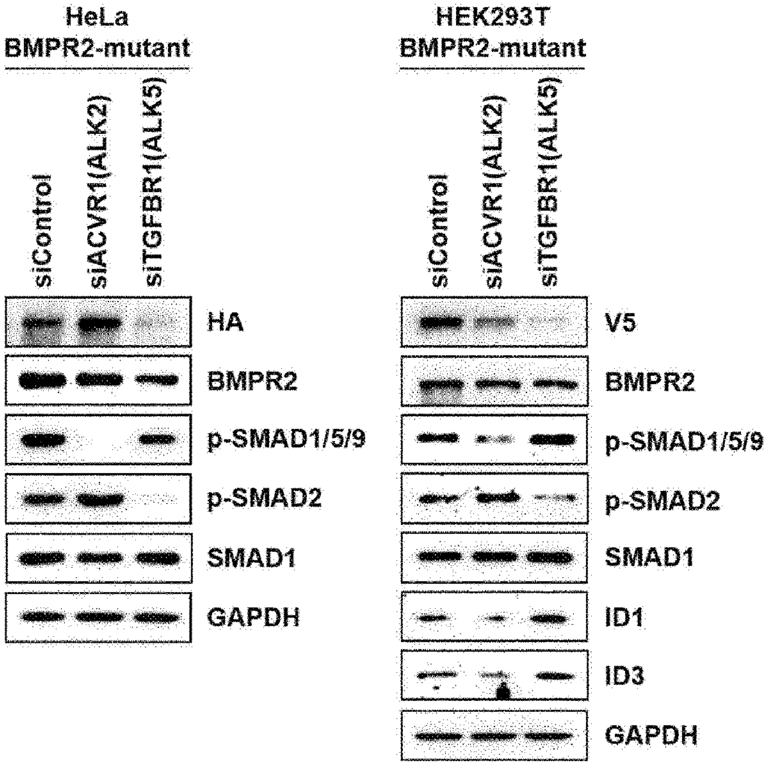
Figure 8A:
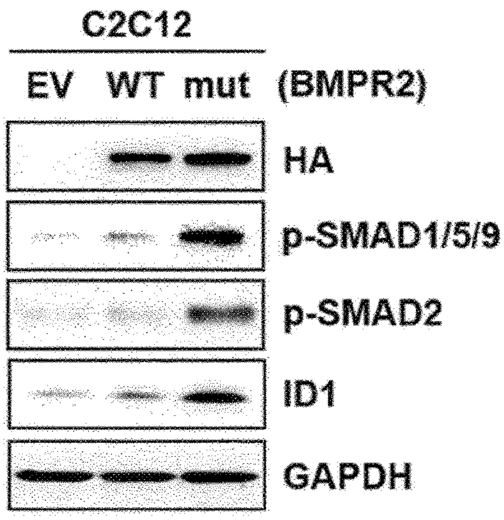
FIGS. 8*a* and 8*b* are photos and graphs showing osteogenic differentiation ability of BMP/SMAD signal hyperactivated by BMPR2 E376K variant in C2C12 cells.
Figure 8B:
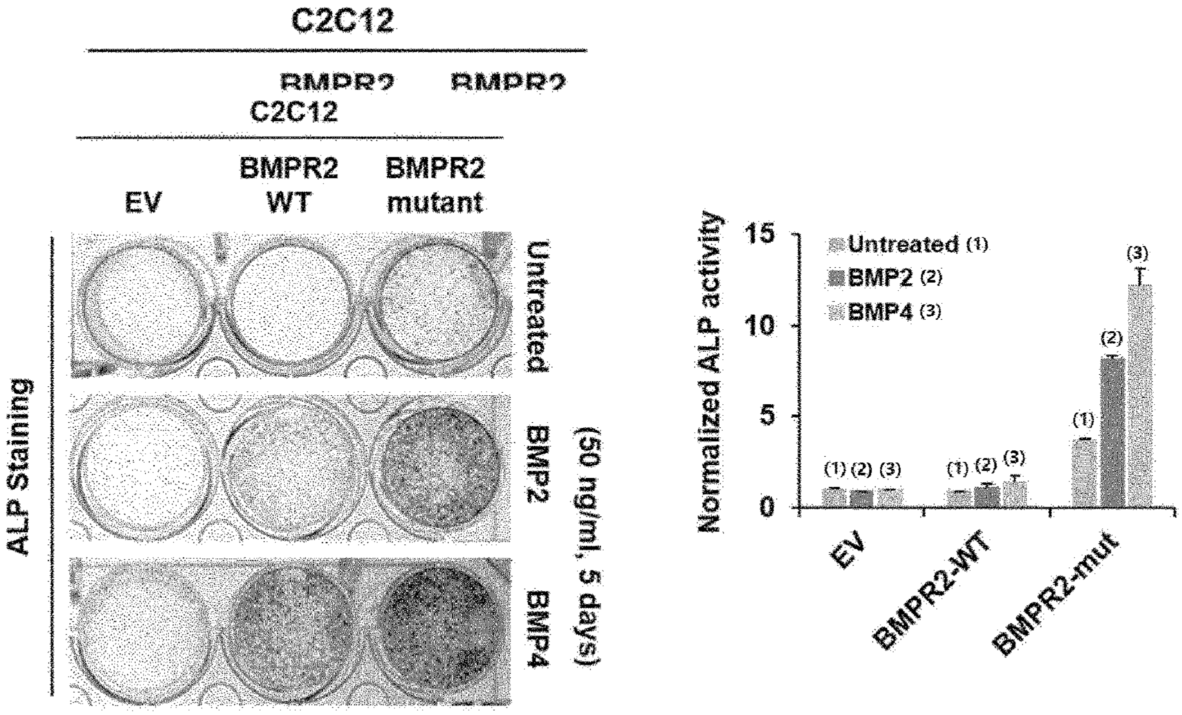

Unlike ACVR1-R206H, it was observed SMAD2 phosphorylation was enhanced in the patient-derived cells (see FIG. if), and also in HEK293T cells expressing BMPR2-E376K, which is not the case in the cells expressing the ACVR1-R206H variant (see FIG. 3*d*). Quantitative mRNA detection confirmed that the expression of the genes downstream is increased (see FIG. 6), implying that SMAD2 phosphorylation due to the BMPR2-E376K variant is indeed functional. In order to specify the type I TGF-beta receptor responsible for SMAD2 activation in the BMPR2-E376K background, individual type I receptors in the patient-derived cells were depleted, and it was found that depletion of TGFBR1 led to abrogation of the SMAD2 phosphorylation in patient-derived cells (see FIG. 3*e*) and also other cells stably expressing the BMPR2-E376K mutant (see FIG. 7). To understand the functional roles of SMAD2 activation in FOP lesions in the cells expressing BMPR2-E376K, mouse myogenic C2C12 cells were used, which are derived from the target tissues of FOP pathogenesis. Through lentiviral transduction, the inventors established C2C12 cell lines which stably express empty vector, WT human BMPR2, or the BMPR2-E376K variant. As expected, SMAD1/5/9 phosphorylation and its downstream target ID1 were detected only in the cells expressing BMPR2-E376K (see FIG. 8). Consistently, cells expressing BMPR2-E376K were positive for ALP staining (see FIG. 3*f*). Addition of BMP2 or BMP4 increased the ALP expression in both BMPR2 WT and BMPR2-E376K backgrounds, and it was clear that BMPR2-E376K cells showed higher ALP expression than BMPR2 WT cells (see FIG. 8). In this setting, it was found that treatment with not only dorsomorphin, a potent inhibitor of BMP signaling (see non-patent document 20), but also with SB431542, a potent inhibitor TGF signaling (see non-patent document 21), reduced ALP staining (see FIG. 3*f* to 3g), suggesting that both BMP and TGF signaling activation are important for the heterotopic ossification phenotype of current FOP case.

Experimental Result 2: Establishment of Cell-derived Induced Pluripotent Stem Cells Including BMPR2-E376K Mutant, Differentiation into Mesenchymal Stem Cells, and Verification of Applicability thereof to Treatment of Bone Diseases Hereinafter, experimental results on the verification of the applicability to the treatment of bone diseases will be described, and the experiments are performed by establishing induced pluripotent stem cells (iPSs or iPSCs) from cells derived from FOP patients due to novel genetic mutations and differentiating iPSs into mesenchymal stem cells (MSCs) in order to induce differentiation of desired tissue cells.

First, the process of producing iPSCs using patient-derived cells is as follows.

Reprogramming factors (human Oct4, Sox2, c-Myc, Klf4, and Lin28 mRNA) were transfected into a normal BJ fibroblast, a fibroblast obtained from a FOP BMPR2-E376K patient, and a fibroblast corrected with genetic scissors. Specifically, a total of $1\times10^6$ fibroblasts (the normal BJ fibroblast, the fibroblast obtained from a FOP BMPR2-E376K patient, and fibroblast corrected with gene scissors) were transformed into a single cell state using 0.5% trypsin EDTA (Invitrogen), and three reprogramming plasmids (pCXLE-hOCT4-shp53, pCXLE-hSK, and pCXLE-hUL) (Addgene, Cambridge, MA, USA)) were transformed into cells by 1 μg each using an electroporator (Neon Transfection System, Invitrogen) under conditions of a pulse voltage of 1650 V, a pulse width of 10 ms, and a pulse number of 3. The next day, cells introduced with a plasmid (transfected cells) were seeded onto a 6-cm culture dish and cultured in a fibroblast culture medium for 5 days. After 5 days, vitronectin was coated on a 6-well plate and then the cells were spread on the 6-well plate at a density of $1\times10^4$ cells/well and cultured in a fibroblast culture medium for 1 day. Vitronectin coating was performed by adding 1 ml of a vitronectin solution (5 μg/ml) to the well and incubating at room temperature for at least 1 hour. The next day, the medium was replaced with TeSR™-E7™ medium, a human iPSC induction medium, and then replaced with fresh TeSR™-E7™ medium every day for about 2-3 weeks. In the process, colonies similar to those of blastocyst-derived embryonic stem cells (ES cells) began to appear. Only the colonies were picked up, and a new dish coated with vitronectin was replaced with TeSR™-E8™ medium (STEMCELL Technology), which is an iPSC culture medium, and was cultured. Accordingly, BJ-WT iPSs, patient-derived BMPR2 mutation iPSs, and gene correction BMPR2-restored iPSs were obtained (see FIGS. 10 and 11).

In order to verify whether the obtained cell colonies are undifferentiated iPSs, fluorescent immunostaining was performed as follows.

In order to identify the undifferentiated state of iPSCs, iPSCs cultured in vitronectin-coated 6 wells for 5 days were washed three times with 1×PBS (WELGENE) and then fixed with 4% paraformaldehyde (PFA, Sigma) for 10 minutes. The iPSCs were washed again with 1×PBS three times for 10 minutes, and then were treated with 10% normal goat serum (NGS) at room temperature for 1 hour. Thereafter, primary antibodies, of which expression is to be identified, was treated in each well with 1% NGS for 1 hour, washed three times with 1×PBS, and then secondary antibodies were treated again for 1 hour. Mouse anti-Oct4 antibodies (1:500 ratio, Santa Cruz Biotechnology Inc., Santa Cruz, CA, USA), mouse anti-SSEA4 antibodies (1:500 ratio, Millipore), mouse anti-Tra1-60 antibodies (1:500 ratio, Millipore), and mouse anti-Tra1-81 antibodies (1:500 ratio, Millipore) were used as human embryonic stem cell-specific antibodies used for fluorescence immunostaining, and Alexa Fluor 594 goat anti-mouse IgGs (1:500 ratio, Invitrogen) were used as the secondary antibodies. After the secondary antibody treatment, cell nuclei were stained with DAPI (4',6-diamidino-2-phenylindole, Sigma) for 5 minutes and observed with a fluorescence microscope. The antibodies were bound in order to identify the expression of iPS markers, Oct4, Sox2, SSEA4, Tral-60, and Tral-81, and then the expression of all iPS markers in the cells were identified through a fluorescence microscope (see FIG. 12).

In addition, cells were collected to obtain RNA, then synthesized into cDNA, and real-time qPCR was performed under the following conditions.

(Ips Markers)

The iPS colonies during stable culture were harvested, mRNA was extracted and synthesized into cDNA, and hOCT4 and hNanog primers were treated, respectively, to confirm results of qPCR. HEK293T was used as a negative control and H9-ESC was used as a positive control.

```
(Chondrogenic marker)
                                (SEQ ID No. 25 and 26)
Human COL2A1_F (5'→3'):
cctggtccccctggtcttgg,

_R:
catcaaatcctccagccatc

(BMP/SMAD target gene)
HumanID1_F (5'→3'):
                                (SEQ ID No. 27 and 28)
AATCATGAAAGTCGCCAGTG,

_R:
ATGTCGTAGAGCAGCACGTTT

HumanID2_F (5'→3'):
                                (SEQ ID No. 29 and 30)
ATGAAAGCCTTCAGTCCCGT,

_R:
TTCCATCTTGCTCACCTTCTT

HumanID3_F (5'→3'):
                                (SEQ ID No. 31 and 32)
TCATCTCCAACGACAAAAGG,

_R:
ACCAGGTTTAGTCTCCAGGAA

(Osteogenic marker)
HumanALP_E (5'→3'):
                                (SEQ ID No. 33 and 34)
AGTGCAGCTCATACTCCATGC,

_R:
GCGGTTCCAGAAGTCCGGGTT

Human Osteocalcin_F (5'→3'):
                                (SEQ ID No. 35 and 36)
cactcctcgccctattggc,

_R:
ccctcctgcttggacacaaag
```

As a result of performing real-time qPCR, it was confirmed that mRNA expression of Oct4 and Nanog, iPS markers, was increased in BJ-WT, BMPR2 mutation, and BMPR2-restored (FOP #203) iPSs which were established (see FIG. 13). As described above, it was verified through the immunofluorescence technique and the qPCR technique that the obtained cell colonies were iPSs.

Next, it was verified whether the differentiation from iPSCs to MSCs was well performed. The differentiation process from the iPSCs into the MSCs is as follows (see FIG. 14).

The undifferentiated iPSCs were reacted with collagenase IV (10 mg/ml, Worthington Biochemical Corporation) for 10 minutes at 37° C. to remove cells from the culture dish, and the cells in the clumpy form were grown in a suspension culture in a 6-cm petri dish (SPL) for 7 days to form embryoid bodies. The culture medium was used in the formation of embryoid bodies, which was supplemented with DMEM/F12, 10% knockout serum replacement, 100 U/ml penicillin-streptomycin, 0.1 mM NEAA, and 0.1 mM beta-mercaptoethanol (all Invitrogen). On day 7 of the formation of the embryoid bodies, the embryoid bodies were inoculated into a culture dish coated with 0.1% gelatin (sigma) and the culture medium was replaced with an MSC differentiation induction medium. The MSC differentiation induction medium was used by adding 2% B27, 1% Insulin-Transferrin-Selenium (ITS), and 1% chemically defined lipid concentrate to MEM-alpha, 10% FBS, and 100 U/ml penicillin-streptomycin (all Invitrogen). It was observed that cells having a shape similar to MSCs were induced on days 7 to 10 through the MSC differentiation induction medium, and about 2 weeks after the differentiation induction, the cells were washed using 1×PBS, then removed using 0.5% Trypsin-EDTA, and then subcultured with the MSC culture medium containing 10% FBS and 100 U/ml penicillin-streptomycin in MEM-alpha to secure MSCs.

In order to verify the established MSCs, expression of CD73, CD90, and CD105, MSC surface markers, was identified by a flow cytometry. The expression of CD45, a negative marker of MSCs, was not identified, and it was verified that the differentiation from iPSs to MSCs were well performed through increased expression of CD73, CD90, and CD105 (see FIG. 15).

Next, the MSCs obtained through the culture were induced to be differentiated into chondrocytes, osteoblasts, and adipocytes, and then the differentiation potential was identified by performing Alcian blue staining, Alizarin Red S staining, and Oil Red O staining as follows.

It was confirmed through the Alcian blue staining that MSCs were inoculated in 24-well with an MSC culture solution by micromass technique, high density dot culture, and then after 2 hours, stably bound to the bottom of the 24-well for the formation of chondrocytes, and in the case of iPSs, a single colony was seeded into each well with a TeSR™-E8™ medium in 48-well, and when the colonies became full in the wells, the medium was replaced with a chondrogenic differentiation medium supplemented with 10% FBS (1% insulin-transferrin-selenium, 0.1 μM dexamethasone, 0.17 mM arscorbic acid-2-phosphate, 0.35 mM proline, and 0.15% glucose), and then a recombinant human BMP2 protein was treated without or with 50 ng/ml and cultured with a fresh medium every 2-3 days for 3 weeks. Then, the cells were fixed with 4% paraformaldehyde for 20 minutes, washed with PBS, and then stained with an Alcian blue 8GX (pH 1.0) solution in the dark. The next day, cells were washed once with 0.1 M HCl and immediately washed twice with PBS, and then colonies stained with blue were identified. Finally, after taking a picture, the dye was extracted by 6 M Guanidine-HCl for 2 hours, and then absorbance was measured at 600 nm using a GloMax® instrument.

Alizarin Red S staining was performed by seeding MSCs established from iPSs into 24-well cell culture plates in 24-well at a density of $8\times10^4$ cells/well and culturing the MSCs at 37° C. under 5% $CO_2$ and 3% $O_2$ conditions in MEM-alpha supplemented with 10% FBS and 1% penicillin-streptomycin. For induction of osteogenic differentiation, when the cell confluency reached 80% to 90%, the original medium was replaced with an osteogenic differentiation medium (10% FBS, 100 nM dexamethasone, 10 mM beta-glycerophosphate, and 50 μM ascorbic acid-2-phosphate) without or with recombinant human BMP2 protein (50 ng/ml). The medium was replaced with a fresh differentiation medium once per 2-3 days, and after 3 weeks, the Alizarin Red S staining was performed to confirm whether it was stained red. Finally, after taking a picture, the dye was dissolved in 10% cetylpyridinium chloride, and then absorbance was measured at 560 nm using the GloMax® instrument.

Oil Red O staining was performed by first seeding MSCs with a 10% MEM-alpha medium into 24-well culture plates in order to identify adipogenic differentiation among the trilineage paraxial mesodermal differentiation capacity of MSCs. When cells exhibit 80% to 90% confluency, they were replaced with adipogenic differentiation medium and cultured for 12-14 days, and the medium was replaced once per 3 days. When differentiated into mature adipocytes, many intracellular lipid vesicles are observed, and thus, a lipophilic dye such as Oil Red O may be used to stain the cells. The cultured cell medium was removed, washed twice with PBS, then fixed for 30 minutes by adding 4% paraformaldehyde, and washed again with distilled water twice. 60% isopropanol was added to each well, removed after 5 minutes incubation, and an Oil Red O working solution (300 mg Oil Red O powder+100 ml 99% isopropanol) was added to completely immerse the cells. After 20 minutes, the cells were washed five times with distilled water, treated with hematoxylin counterstain for 1 minute, and then washed again five times with warm tap water. Finally, after the adipocytes stained with red were identified, a photograph was taken.

As a result of the identification using the staining technique, it was found that the BJ-WT, BMPR2 mutation, and BMPR2 restored MSCs were well differentiated into chondrocytes, osteoblasts, and adipocytes (see FIG. 16). Accordingly, it was confirmed that the MSCs obtained from iPSs were well established.

The protein expression of the BMP/SMAD signaling factor was identified using the iPSs and MSCs thus obtained. In the case of patient-derived cells (BMPR2 mutation), it was confirmed that the phosphorylation of SMAD1/5/9 and SMAD2 was increased in iPSs and MSCs as well as the protein expression identified in fibroblasts, and the expression of ID1 and ID3, which are target genes of SMAD1/5/9, was also increased. In addition, it was found that BMP/SMAD activity was inhibited in fibroblast, iPS, and MSC cells in which the BMPR2-E376K mutation was corrected (BMPR2-restored) with CRISPR-Cas9 as in normal cell lines (BJ-WT) (see FIG. 17). Accordingly, it was possible to establish iPS and MSC cell lines that have the same function as fibroblast and additionally have pluripotency.

Next, in order to identify chondrogenic differentiation capability in BJ-WT, BMPR2 mutation, and BMPR2-restored iPSs, iPS cells were cultured in the chondrogenic differentiation medium containing BMP2 recombinant proteins that help to promote chondrogenic differentiation for 3 weeks, and the mRNA expression levels of the cells were identified by qPCR. The increase in expression of Col2a1, a chondrogenic differentiation marker, in a BMPR2 mutation was decreased again in BMPR2-restored iPSs (see FIG. 18).

In addition, as a result of identifying chondrogenic differentiation levels using the Alcian blue staining, it was found that BMPR2 mutation iPSs were stained with dark blue when the cells were cultured in the chondrogenic differentiation medium to which BMPR2 was added, and BMPR2-restored iPSs in which BMPR2 mutation was corrected had a weak chondrogenic differentiation level like BJ-WT (see FIG. 19). Accordingly, it was verified that the chondrogenic differentiation capability of established iPSs exhibited similar results as in fibroblast.

As a result of checking, by qPCR, the expression levels of mRNA of ID1-ID3, which are BMP/SMAD1/5/9 target genes, in BJ-WT, BMPR2 mutation, and BMPR2-restored MSCs obtained from iPSs, it was confirmed that similar to the result of fibroblast, the expression of BMPR2 mutation increased and the expression decreased again in BMPR2-restored MSCs, thereby showing a result similar to BJ-WT (see FIG. 20).

In addition, it was confirmed that when BMP2 was treated when chondrogenic differentiation was induced using MSCs, the degree of staining in BMPR2 mutation MSCs increased compared to BJ-WT, but when chondrogenic differentiation was induced without BMP2 treatment, the chondrogenic differentiation was more strongly induced in the BMPR2 mutation. In addition, it was confirmed that the chondrogenic differentiation was recovered to a normal level in the BMPR2-restored MSCs (see FIG. 21).

As a result of identifying osteogenic differentiation levels by the Alizarin Red S staining using MSCs cultured in the osteogenic differentiation medium for 3 weeks, it was confirmed that calcium deposits were significantly increased in BMPR2 mutation MSCs regardless of BMP2 treatment and recovered to a normal level in BMPR2-restored MSCs (see FIG. 22).

Finally, as a result of identifying, by qPCR, mRNA levels of ALP and Osteocalcin expressed in the osteogenic differentiation step, it was confirmed that the expression increased in the BMPR2 mutation MSCs and recovered in the BMPR2-restored MSCs (see FIG. 23).

The present invention reports that a gain-of-function mutation in the BMPR2 gene is causative for an inherited skeletal dysplasia, FOP, characterized by heterotopic bone formation in places where soft tissue should grow. To date, ACVR1 is the only known gene responsible for FOP, and more than 95% of FOP patients harbor the specific R206H mutation in the ACVR1 gene (see non-patent documents 6 and 7). However, due to the limited genetic causes identified in FOP patients, it is not yet clear how ACVR1-R206H induces constitutive activation of BMP signals and the pathophysiology of FOP in general. In the present invention, it was described that an individual presented with typical FOP phenotypes, except for the big toe anomaly. From the genetic sequencing analysis, it was found that the individual did not have a mutation in ACVR1, but instead harbored a novel gain-of-function mutation in the BMPR2 gene. The pathogenicity of the BMPR2-E376K mutation was validated with multiple functional assays, and the inventors found several interesting aspects of the BMPR2-E376K mutation, which will be informative to understand not only the pathogenesis of FOP, but the nature of TGF/BMP signaling cascades as well.

The inventors found that BMPR2-E376K variant is consistently associated with the type I receptor ACVR1, which increases the proximity between type I and type II TGF-beta receptors even in the absence of BMP ligands (see FIG. 3*a*). The molecular consequences of the ACVR1-R206H mutant remain elusive. Interestingly, it was found that combined expression of ACVR1-R206H and BMPR2-E376K showed additive effects (see FIG. 3*b*) on inducing BMP signals, implying that ACVR1-R206H might have different molecular mechanisms of activation of BMP signaling cascades. Nonetheless, the inventors believe that these findings will be not only informative to understand the exact pathophysiology of FOP arising from the ACVR1-R206H mutation, but also useful to develop drugs that inhibit enhanced BMP signaling, which will be applicable to FOP and other diseases as well.

It was reported that treatment with activin A in the presence of the ACVR1-R206H mutant further stimulates SMAD1/5/9 phosphorylation (see non-patent documents 11 and 12). To date, there is no explanation for the activation of BMP signals in the ACVR1-R206H background, although activin A is normally known to induce TGF-beta signaling. The inventors demonstrated that the BMPR2-E376K mutant and the ACVR1-R206H mutant have a different molecular basis for inducing BMP signals. However, similar to ACVR1-R206H, it was found that BMPR2-E376K is also able to further induce BMP signals upon activin A treatment (see FIG. 3*c*). These findings suggest that the molecular mechanisms of enhanced BMP signaling in response to activin A in FOP could be more general rather than depending on specific molecular backgrounds. Our findings will be informative for understanding the functional roles of activin A in FOP, although further studies will be required.

Loss-of-function mutations of BMPR2 have been well described in pulmonary artery hypertension (PAH) (see non-patent documents 22 and 23). It was proposed that loss of BMPR2 function results in enhanced TGF-beta signaling cascades, leading to hyperproliferation of smooth muscle cells in blood vessels, although the exact molecular basis of PAH remains elusive (see non-patent document 24). Here the inventors report the first gain-of-function BMPR2 mutation and its potentially causative role in human disease. These findings clearly demonstrate that the constitutive activation of BMPR2 enhances BMP signaling, which results in heterotopic bone formation phenotype. Understanding of the physiological functions of BMPR2 will also contribute to our understanding of the pathophysiology of PAH, and set the stage for developing new treatment options.

Unlike the ACVR1-R206H mutant, cells expressing BMPR2-E376K showed SMAD2 phosphorylation and downstream target gene expression. In further studies, it was identified that the type I receptor responsible for SMAD2 phosphorylation is TGFBR1, suggesting that in some cases there might be crosstalk between BMP and TGF signaling. It was also found that the activated SMAD2-dependent signaling is partly involved in the processes of heterotopic ossification, which is supported by other studies showing that TGF-beta signaling is critical for FOP phenotypes (see non-patent document 25). It will be worth trying novel therapeutic approaches with FOP that focus on inhibiting TGF-beta signaling.

In addition, it was confirmed herein that, in order to verify the pathogenicity of FOP, mutation of the BMPR2 gene was corrected to a normal state using a gene scissors technique, and then the osteogenic differentiation level was restored to a normal phenotype. Furthermore, fibroblasts obtained from FOP patients for the treatment of bone diseases were corrected with genetic scissors, and then differentiated into induced pluripotent stem cells (iPSs) using reprogramming factors such as Oct4, Sox2, c-Myc, Klf4, and Lin28. iPSs are induced pluripotent stem cells that can be differentiated into various tissue cells, and this technology can be said to prepare the ground for screening a therapeutic agent for abnormal osteogenic diseases. In addition, normal stem cells can be obtained by correcting the genetic mutation of the patient and be utilized in cell therapy. However, since the amount of iPSs obtained is too small to be actually applied to the treatment, in order to compensate for this, using mesenchymal stem cells (MSCs) having high proliferation and differentiation efficiency, a sufficient amount of cells can be applied to the treatment.

Although the exemplary embodiments of the present invention have been described in order to achieve the technical objectives, it is understood that various changes and modifications can be made by one with ordinary skilled in the art within the spirit and scope of the present invention as hereinafter claimed.

SEQUENCE LISTING

```
<160> NUMBER OF SEQ ID NOS: 69

<210> SEQ ID NO 1
<211> LENGTH: 53
<212> TYPE: DNA
<213> ORGANISM: Artificial Sequence
<220> FEATURE:
<223> OTHER INFORMATION: BMPR2-F Primer

<400> SEQUENCE: 1

ggggacaagt ttgtacaaaa aagcaggctt aatgacttcc tcgctgcagc ggc            53


<210> SEQ ID NO 2
<211> LENGTH: 48
<212> TYPE: DNA
<213> ORGANISM: Artificial Sequence
<220> FEATURE:
<223> OTHER INFORMATION: BMPR2-R Primer

<400> SEQUENCE: 2

ggggaccact ttgtacaaga aagctgggtc tcacagacag ttcattcc                  48


<210> SEQ ID NO 3
<211> LENGTH: 23
<212> TYPE: DNA
<213> ORGANISM: Artificial Sequence
<220> FEATURE:
<223> OTHER INFORMATION: Target sequence for CRISPR-Cas9

<400> SEQUENCE: 3

agataatgca gccataagca agg                                             23


<210> SEQ ID NO 4
<211> LENGTH: 120
<212> TYPE: DNA
<213> ORGANISM: Artificial Sequence
<220> FEATURE:
<223> OTHER INFORMATION: donor template

<400> SEQUENCE: 4

ccatgaggct gactggaaat agactggtgc gcccagggga ggaagataat gcagccatct     60

ccgaggtgag tgtatacaaa aggtatcaca ctgatgtact ttgaaatgat aatttaatta    120


<210> SEQ ID NO 5
<211> LENGTH: 20
<212> TYPE: DNA
<213> ORGANISM: Artificial Sequence
<220> FEATURE:
<223> OTHER INFORMATION: hBMPR2 E7 F1

<400> SEQUENCE: 5

gcctcctttt acagccctat                                                 20


<210> SEQ ID NO 6
<211> LENGTH: 20
<212> TYPE: DNA
<213> ORGANISM: Artificial Sequence
<220> FEATURE:
<223> OTHER INFORMATION: hBMPR2 E7 R1

<400> SEQUENCE: 6
```

aactttaccc ttgcctcaaa 20

<210> SEQ ID NO 7
<211> LENGTH: 51
<212> TYPE: DNA
<213> ORGANISM: Artificial Sequence
<220> FEATURE:
<223> OTHER INFORMATION: hBMPR2 E7 dF1

<400> SEQUENCE: 7
acactctttc cctacacgac gctcttccga tctacagcag aaatgtccta g 51

<210> SEQ ID NO 8
<211> LENGTH: 52
<212> TYPE: DNA
<213> ORGANISM: Artificial Sequence
<220> FEATURE:
<223> OTHER INFORMATION: hBMPR2 E7 dR1

<400> SEQUENCE: 8
gtgactggag ttcagacgtg tgctcttccg atctctcttt accttaggtg at 52

<210> SEQ ID NO 9
<211> LENGTH: 21
<212> TYPE: DNA
<213> ORGANISM: Artificial Sequence
<220> FEATURE:
<223> OTHER INFORMATION: mCol2a1 sense primer

<400> SEQUENCE: 9
cctccgtcta ctgtccactg a 21

<210> SEQ ID NO 10
<211> LENGTH: 20
<212> TYPE: DNA
<213> ORGANISM: Artificial Sequence
<220> FEATURE:
<223> OTHER INFORMATION: mCol2a1 antisense primer

<400> SEQUENCE: 10
attggagccc tggatgagca 20

<210> SEQ ID NO 11
<211> LENGTH: 20
<212> TYPE: DNA
<213> ORGANISM: Artificial Sequence
<220> FEATURE:
<223> OTHER INFORMATION: mCol0a1 sense primer

<400> SEQUENCE: 11
aacaggtatg cccgtgtctg 20

<210> SEQ ID NO 12
<211> LENGTH: 20
<212> TYPE: DNA
<213> ORGANISM: Artificial Sequence
<220> FEATURE:
<223> OTHER INFORMATION: mCol0a1 antisense primer

<400> SEQUENCE: 12
tcatcaaatg ggatgggggc 20

<210> SEQ ID NO 13
<211> LENGTH: 20
<212> TYPE: DNA
<213> ORGANISM: Artificial Sequence
<220> FEATURE:
<223> OTHER INFORMATION: mAggrecan sense primer

<400> SEQUENCE: 13
tggcttctgg agacaggact 20

<210> SEQ ID NO 14
<211> LENGTH: 20
<212> TYPE: DNA
<213> ORGANISM: Artificial Sequence
<220> FEATURE:
<223> OTHER INFORMATION: mAggrecan antisense primer

<400> SEQUENCE: 14
ttctgctgtc tgggtctcct 20

<210> SEQ ID NO 15
<211> LENGTH: 23
<212> TYPE: DNA
<213> ORGANISM: Artificial Sequence
<220> FEATURE:
<223> OTHER INFORMATION: mGapdh sense primer

<400> SEQUENCE: 15
catgttccag tatgactcca ctc 23

<210> SEQ ID NO 16
<211> LENGTH: 20
<212> TYPE: DNA
<213> ORGANISM: Artificial Sequence
<220> FEATURE:
<223> OTHER INFORMATION: mGapdh antisense primer

<400> SEQUENCE: 16
ggcctcaccc catttgatgt 20

<210> SEQ ID NO 17
<211> LENGTH: 19
<212> TYPE: DNA
<213> ORGANISM: Artificial Sequence
<220> FEATURE:
<223> OTHER INFORMATION: hPAl-1 sense primer

<400> SEQUENCE: 17
tcctggttct gcccaagtt 19

<210> SEQ ID NO 18
<211> LENGTH: 20
<212> TYPE: DNA
<213> ORGANISM: Artificial Sequence
<220> FEATURE:
<223> OTHER INFORMATION: hPAl-1 antisense primer

<400> SEQUENCE: 18
ccaggttctc taggggcttc 20

<210> SEQ ID NO 19
<211> LENGTH: 20
<212> TYPE: DNA
<213> ORGANISM: Artificial Sequence
<220> FEATURE:
<223> OTHER INFORMATION: hPDGFB sense primer

<400> SEQUENCE: 19
ctggcatgca agtgtgagac 20

<210> SEQ ID NO 20
<211> LENGTH: 19
<212> TYPE: DNA
<213> ORGANISM: Artificial Sequence
<220> FEATURE:
<223> OTHER INFORMATION: hPDGFB antisense primer

<400> SEQUENCE: 20
cgaatggtca cccgagttt 19

<210> SEQ ID NO 21
<211> LENGTH: 20
<212> TYPE: DNA
<213> ORGANISM: Artificial Sequence
<220> FEATURE:
<223> OTHER INFORMATION: hTHBS-1 sense primer

<400> SEQUENCE: 21
caatgccaca gttcctgatg 20

<210> SEQ ID NO 22
<211> LENGTH: 18
<212> TYPE: DNA
<213> ORGANISM: Artificial Sequence
<220> FEATURE:
<223> OTHER INFORMATION: hTHBS-1 antisense primer

<400> SEQUENCE: 22
tggagaccag ccatcgtc 18

<210> SEQ ID NO 23
<211> LENGTH: 19
<212> TYPE: DNA
<213> ORGANISM: Artificial Sequence
<220> FEATURE:
<223> OTHER INFORMATION: hGAPDH sense primer

<400> SEQUENCE: 23
agccacatcg ctcagacac 19

<210> SEQ ID NO 24
<211> LENGTH: 19
<212> TYPE: DNA
<213> ORGANISM: Artificial Sequence
<220> FEATURE:
<223> OTHER INFORMATION: hGAPDH antisense primer

<400> SEQUENCE: 24
gcccaatacg accaaatcc 19

<210> SEQ ID NO 25
<211> LENGTH: 20
<212> TYPE: DNA
<213> ORGANISM: Artificial Sequence
<220> FEATURE:
<223> OTHER INFORMATION: Human COL2A1 Forward Primer

<400> SEQUENCE: 25
cctggtcccc ctggtcttgg 20

<210> SEQ ID NO 26
<211> LENGTH: 20
<212> TYPE: DNA
<213> ORGANISM: Artificial Sequence
<220> FEATURE:
<223> OTHER INFORMATION: Human COL2A1 Reverse Primer

<400> SEQUENCE: 26
catcaaatcc tccagccatc 20

<210> SEQ ID NO 27
<211> LENGTH: 20
<212> TYPE: DNA
<213> ORGANISM: Artificial Sequence
<220> FEATURE:
<223> OTHER INFORMATION: Human ID1 Forward Primer

<400> SEQUENCE: 27
aatcatgaaa gtcgccagtg 20

<210> SEQ ID NO 28
<211> LENGTH: 21
<212> TYPE: DNA
<213> ORGANISM: Artificial Sequence
<220> FEATURE:
<223> OTHER INFORMATION: Human ID1 Reverse Primer

<400> SEQUENCE: 28
atgtcgtaga gcagcacgtt t 21

<210> SEQ ID NO 29
<211> LENGTH: 20
<212> TYPE: DNA
<213> ORGANISM: Artificial Sequence
<220> FEATURE:
<223> OTHER INFORMATION: Human ID2 Forward Primer

<400> SEQUENCE: 29
atgaaagcct tcagtcccgt 20

<210> SEQ ID NO 30
<211> LENGTH: 21
<212> TYPE: DNA
<213> ORGANISM: Artificial Sequence
<220> FEATURE:
<223> OTHER INFORMATION: Human ID2 Reverse Primer

<400> SEQUENCE: 30
ttccatcttg ctcaccttct t 21

<210> SEQ ID NO 31
<211> LENGTH: 20
<212> TYPE: DNA
<213> ORGANISM: Artificial Sequence
<220> FEATURE:
<223> OTHER INFORMATION: Human ID3 Forward Primer

<400> SEQUENCE: 31
tcatctccaa cgacaaaagg 20

<210> SEQ ID NO 32
<211> LENGTH: 21
<212> TYPE: DNA
<213> ORGANISM: Artificial Sequence
<220> FEATURE:
<223> OTHER INFORMATION: Human ID3 Reverse Primer

<400> SEQUENCE: 32
accaggttta gtctccagga a 21

<210> SEQ ID NO 33

<211> LENGTH: 21
<212> TYPE: DNA
<213> ORGANISM: Artificial Sequence
<220> FEATURE:
<223> OTHER INFORMATION: Human ALP Forward Primer

<400> SEQUENCE: 33
agtgcagctc atactccatg c 21

<210> SEQ ID NO 34
<211> LENGTH: 21
<212> TYPE: DNA
<213> ORGANISM: Artificial Sequence
<220> FEATURE:
<223> OTHER INFORMATION: Human ALP Reverse Primer

<400> SEQUENCE: 34
gcggttccag aagtccgggt t 21

<210> SEQ ID NO 35
<211> LENGTH: 19
<212> TYPE: DNA
<213> ORGANISM: Artificial Sequence
<220> FEATURE:
<223> OTHER INFORMATION: Human Osteocalcin Forward Primer

<400> SEQUENCE: 35
cactcctcgc cctattggc 19

<210> SEQ ID NO 36
<211> LENGTH: 21
<212> TYPE: DNA
<213> ORGANISM: Artificial Sequence
<220> FEATURE:
<223> OTHER INFORMATION: Human Osteocalcin Reverse Primer

<400> SEQUENCE: 36
ccctcctgct tggacacaaa g 21

Figure 1C:
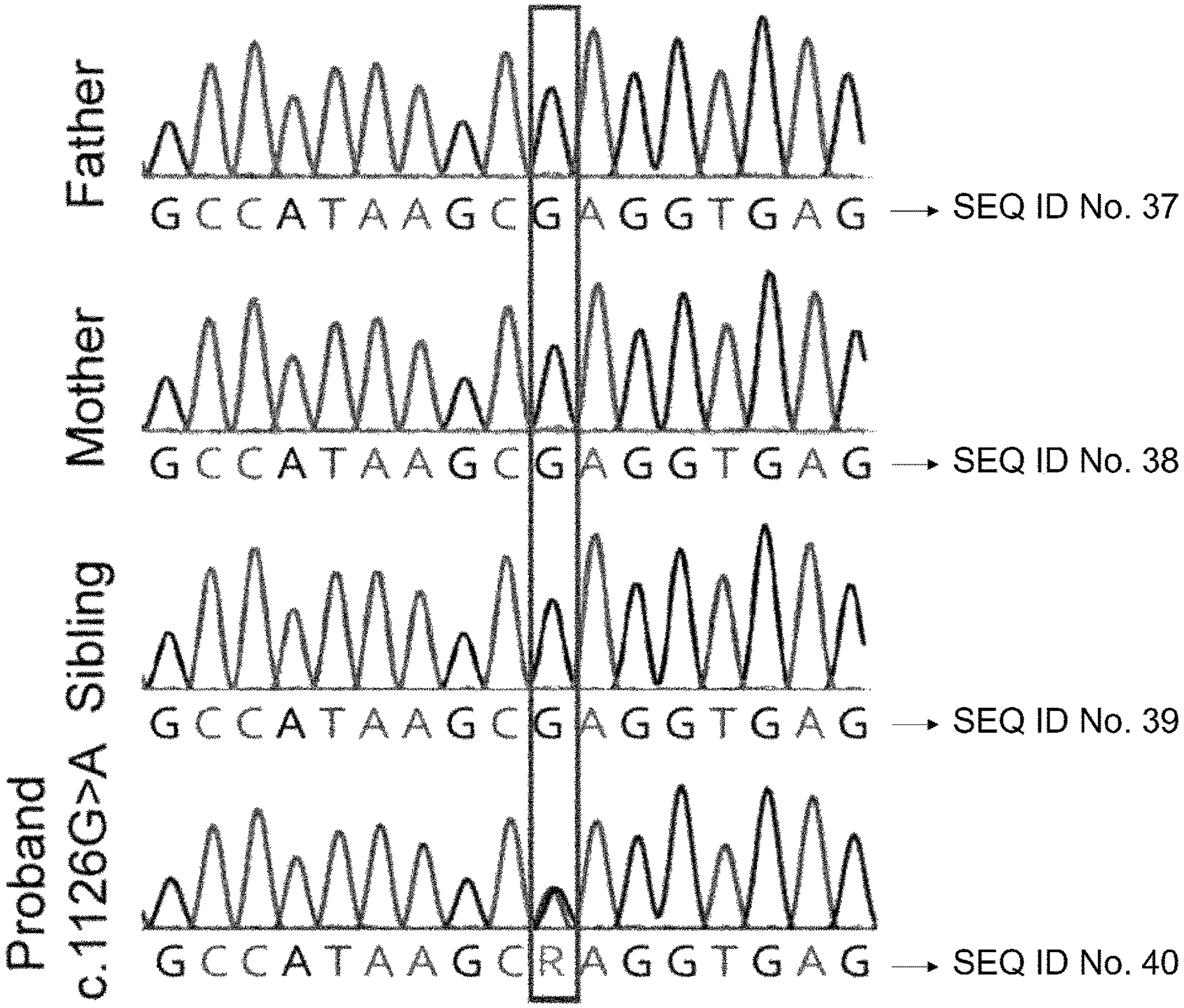
Figure 1D:
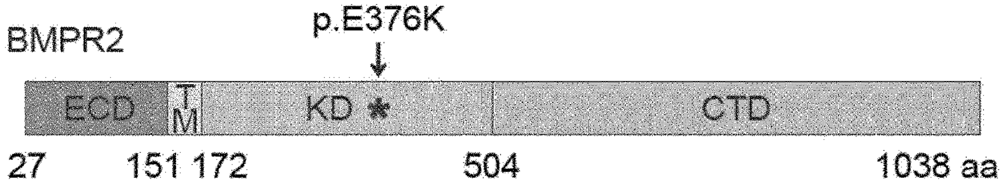
Figure 1G:
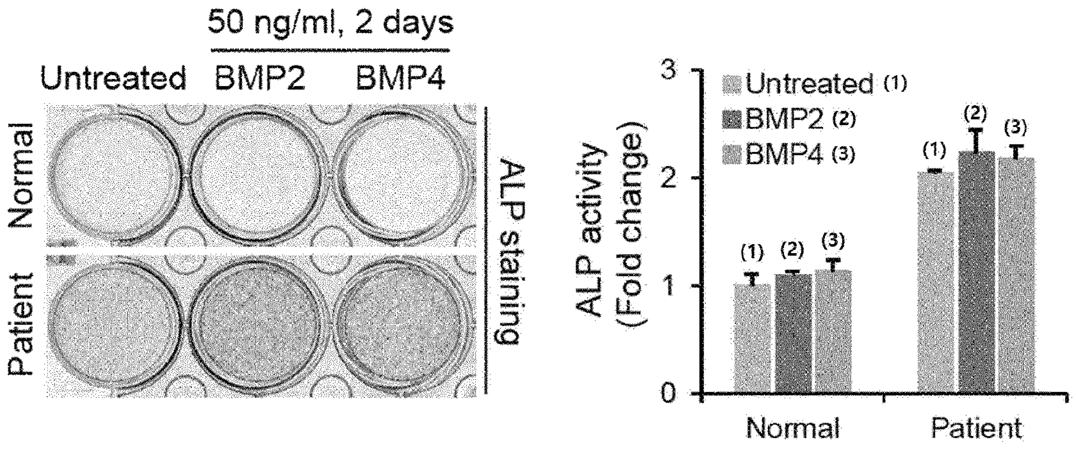
Figure 1H:
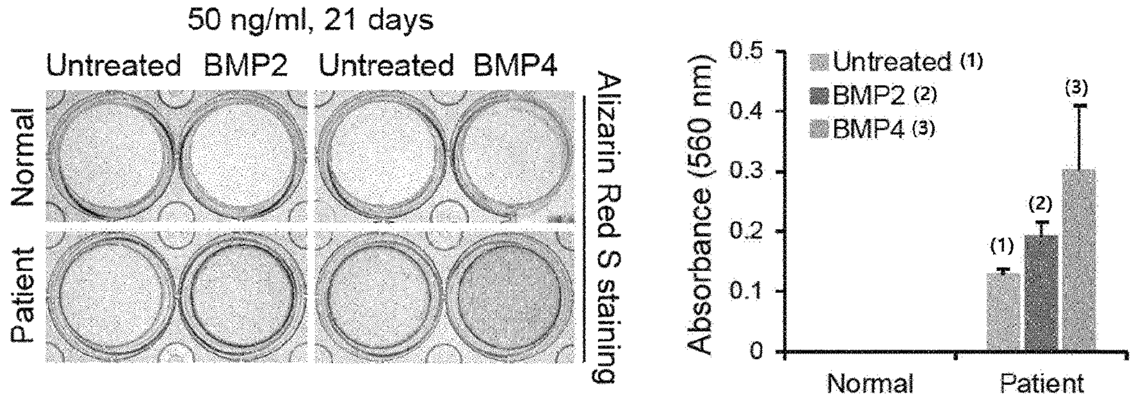

<210> SEQ ID NO 37
<211> LENGTH: 17
<212> TYPE: DNA
<213> ORGANISM: Artificial Sequence
<220> FEATURE:
<223> OTHER INFORMATION: FIG. 1c_Father

<400> SEQUENCE: 37
gccataagcg aggtgag 17

<210> SEQ ID NO 38
<211> LENGTH: 17
<212> TYPE: DNA
<213> ORGANISM: Artificial Sequence
<220> FEATURE:
<223> OTHER INFORMATION: FIG. 1c_Mother

<400> SEQUENCE: 38
gccataagcg aggtgag 17

<210> SEQ ID NO 39
<211> LENGTH: 17
<212> TYPE: DNA
<213> ORGANISM: Artificial Sequence
<220> FEATURE:
<223> OTHER INFORMATION: FIG. 1c_Sibling

<400> SEQUENCE: 39
gccataagcg aggtgag 17

<210> SEQ ID NO 40
<211> LENGTH: 17
<212> TYPE: DNA
<213> ORGANISM: Artificial Sequence
<220> FEATURE:
<223> OTHER INFORMATION: FIG. 1c_Proband_c.1126G>A

<400> SEQUENCE: 40
gccataagcr aggtgag 17

<210> SEQ ID NO 41
<211> LENGTH: 20
<212> TYPE: PRT
<213> ORGANISM: Artificial Sequence
<220> FEATURE:
<223> OTHER INFORMATION: FIG. 1e_BMPR2_Patient

<400> SEQUENCE: 41

Asn Arg Leu Val Arg Pro Gly Glu Glu Asp Asn Ala Ala Ile Ser Lys
1 5 10 15

Val Gly Thr Ile
20

<210> SEQ ID NO 42
<211> LENGTH: 20
<212> TYPE: PRT
<213> ORGANISM: Artificial Sequence
<220> FEATURE:
<223> OTHER INFORMATION: FIG. 1e_BMPR2_Homo sapiens

<400> SEQUENCE: 42

Asn Arg Leu Val Arg Pro Gly Glu Glu Asp Asn Ala Ala Ile Ser Glu
1 5 10 15

Val Gly Thr Ile
20

<210> SEQ ID NO 43
<211> LENGTH: 20
<212> TYPE: PRT
<213> ORGANISM: Artificial Sequence
<220> FEATURE:
<223> OTHER INFORMATION: FIG. 1e_BMPR2_Mus musculus

<400> SEQUENCE: 43

Asn Arg Leu Val Arg Pro Gly Glu Glu Asp Asn Ala Ala Ile Ser Glu
1 5 10 15

Val Gly Thr Ile
20

<210> SEQ ID NO 44
<211> LENGTH: 20
<212> TYPE: PRT
<213> ORGANISM: Artificial Sequence
<220> FEATURE:
<223> OTHER INFORMATION: FIG. 1e_BMPR2_Rattus norvegicus

<400> SEQUENCE: 44

Asn Arg Leu Val Arg Pro Gly Glu Glu Asp Asn Ala Ala Ile Ser Glu
1 5 10 15

Val Gly Thr Ile
20

<210> SEQ ID NO 45
<211> LENGTH: 20
<212> TYPE: PRT
<213> ORGANISM: Artificial Sequence
<220> FEATURE:
<223> OTHER INFORMATION: FIG. 1e_BMPR2_Bos taurus

<400> SEQUENCE: 45

Asn Arg Leu Val Arg Pro Gly Glu Glu Asp Asn Ala Ala Ile Ser Glu
1 5 10 15

Val Gly Thr Ile
20

<210> SEQ ID NO 46
<211> LENGTH: 20
<212> TYPE: PRT
<213> ORGANISM: Artificial Sequence
<220> FEATURE:
<223> OTHER INFORMATION: FIG. 1e_BMPR2_Gallus gallus

<400> SEQUENCE: 46

Asn Arg Leu Val Arg Pro Gly Glu Glu Asp Asn Ala Ala Ile Ser Glu
1 5 10 15

Val Gly Thr Ile
20

<210> SEQ ID NO 47
<211> LENGTH: 20
<212> TYPE: PRT
<213> ORGANISM: Artificial Sequence
<220> FEATURE:
<223> OTHER INFORMATION: FIG. 1e_BMPR2_Callithrix jacchus

<400> SEQUENCE: 47

Asn Arg Leu Val Arg Pro Gly Glu Glu Asp Asn Ala Ala Ile Ser Glu
1 5 10 15

Val Gly Thr Ile
20

<210> SEQ ID NO 48
<211> LENGTH: 20
<212> TYPE: PRT
<213> ORGANISM: Artificial Sequence
<220> FEATURE:
<223> OTHER INFORMATION: FIG. 1e_BMPR2_Sus scrofa

<400> SEQUENCE: 48

Asn Arg Leu Val Arg Pro Gly Glu Glu Asp Asn Ala Ala Ile Ser Glu
1 5 10 15

Val Gly Thr Ile
20

<210> SEQ ID NO 49
<211> LENGTH: 24
<212> TYPE: DNA
<213> ORGANISM: Artificial Sequence
<220> FEATURE:
<223> OTHER INFORMATION: FIG. 2a_mutant

<400> SEQUENCE: 49
gcagccataa gcaaggtgag tgta 24

<210> SEQ ID NO 50
<211> LENGTH: 24

<212> TYPE: DNA
<213> ORGANISM: Artificial Sequence
<220> FEATURE:
<223> OTHER INFORMATION: FIG. 2a_WT

<400> SEQUENCE: 50
gcagccataa gcgaggtgag tgta 24

<210> SEQ ID NO 51
<211> LENGTH: 24
<212> TYPE: DNA
<213> ORGANISM: Artificial Sequence
<220> FEATURE:
<223> OTHER INFORMATION: FIG. 2a_WT

<400> SEQUENCE: 51
gcagccataa gcgaggtgag tgta 24

<210> SEQ ID NO 52
<211> LENGTH: 24
<212> TYPE: DNA
<213> ORGANISM: Artificial Sequence
<220> FEATURE:
<223> OTHER INFORMATION: FIG. 2a_KO #3
<220> FEATURE:
<221> NAME/KEY: misc_difference
<222> LOCATION: (9)..(9)
<223> OTHER INFORMATION: replace= "-" for a deletion

<400> SEQUENCE: 52
gcagccataa gcaaggtgag tgta 24

<210> SEQ ID NO 53
<211> LENGTH: 24
<212> TYPE: DNA
<213> ORGANISM: Artificial Sequence
<220> FEATURE:
<223> OTHER INFORMATION: FIG. 2a_WT

<400> SEQUENCE: 53
gcagccataa gcgaggtgag tgta 24

<210> SEQ ID NO 54
<211> LENGTH: 25
<212> TYPE: DNA
<213> ORGANISM: Artificial Sequence
<220> FEATURE:
<223> OTHER INFORMATION: FIG. 2a_KO #5

<400> SEQUENCE: 54
gcagccataa agcaaggtga gtgta 25

<210> SEQ ID NO 55
<211> LENGTH: 24
<212> TYPE: DNA
<213> ORGANISM: Artificial Sequence
<220> FEATURE:
<223> OTHER INFORMATION: FIG. 2a_WT

<400> SEQUENCE: 55
gcagccataa gcgaggtgag tgta 24

<210> SEQ ID NO 56
<211> LENGTH: 24
<212> TYPE: DNA
<213> ORGANISM: Artificial Sequence
<220> FEATURE:

<223> OTHER INFORMATION: FIG. 2a_KI #203

<400> SEQUENCE: 56
gcagccatct ccgaggtgag tgta 24

<210> SEQ ID NO 57
<211> LENGTH: 5
<212> TYPE: PRT
<213> ORGANISM: Artificial Sequence
<220> FEATURE:
<223> OTHER INFORMATION: FIG. 2a_mutant_PRT

<400> SEQUENCE: 57

Ala Ala Ile Ser Lys
1 5

<210> SEQ ID NO 58
<211> LENGTH: 5
<212> TYPE: PRT
<213> ORGANISM: Artificial Sequence
<220> FEATURE:
<223> OTHER INFORMATION: FIG. 2a_WT_PRT

<400> SEQUENCE: 58

Ala Ala Ile Ser Glu
1 5

<210> SEQ ID NO 59
<211> LENGTH: 5
<212> TYPE: PRT
<213> ORGANISM: Artificial Sequence
<220> FEATURE:
<223> OTHER INFORMATION: FIG. 2a_KO #3_PRT

<400> SEQUENCE: 59

Ala Ala Ile Ala Arg
1 5

<210> SEQ ID NO 60
<211> LENGTH: 5
<212> TYPE: PRT
<213> ORGANISM: Artificial Sequence
<220> FEATURE:
<223> OTHER INFORMATION: FIG. 2a_KO #5_PRT

<400> SEQUENCE: 60

Ala Ala Ile Lys Gln
1 5

<210> SEQ ID NO 61
<211> LENGTH: 5
<212> TYPE: PRT
<213> ORGANISM: Artificial Sequence
<220> FEATURE:
<223> OTHER INFORMATION: FIG. 2a_KI #203_PRT

<400> SEQUENCE: 61

Ala Ala Ile Ser Glu
1 5

Figure 4A:
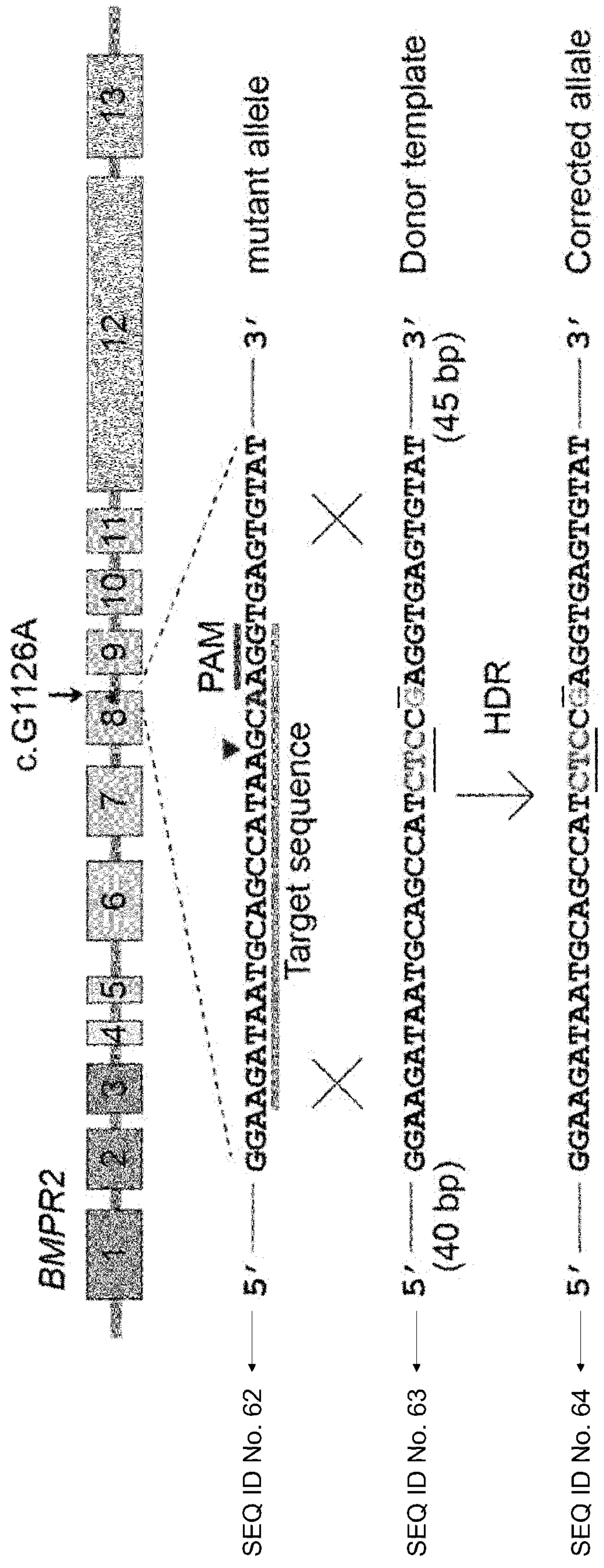
FIGS. 4*a* to 4*c* are Scheme of BMPR2 genomic DNA editing induced by CRISPR-Cas9 in patient-derived fibroblasts. A plus strand single-guide RNA (sgRNA, bold underline) sequence targeting BMPR2 exon 8 in the region that corresponds to G to A missense mutation site was designed adjacent to a Protospacer Adjacent Motif (PAM, bold upper line). Precise cleavage of the third nucleotide (an arrowhead) from PAM by RNA-guided Cas9 induce double-strand breaks (DSB) in the BMPR2 mutant allele. The DSB is repaired by one of two general repair pathways: homology directed repair (HDR) and non-homologous end joining (NHEJ).
Figure 5A:
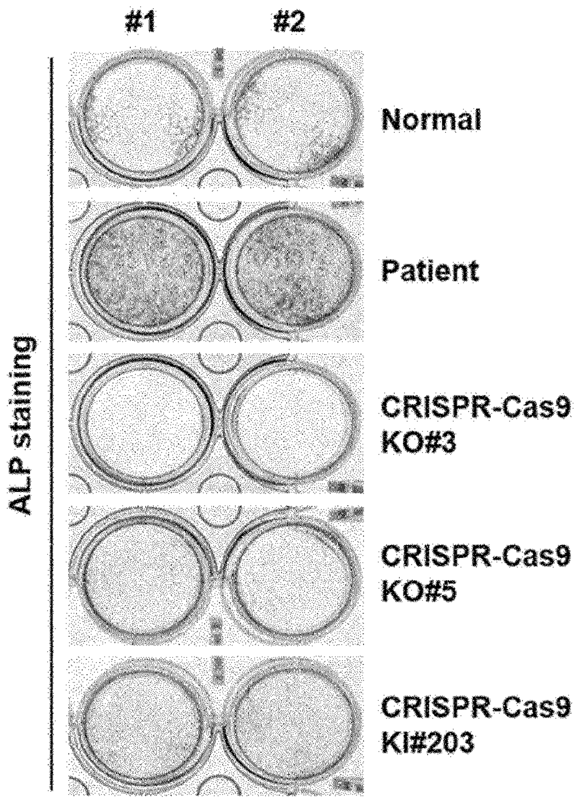
FIGS. 5*a* and 5*b* are photos showing results of staining for detection of osteogenic differentiation. Duplicate samples (#1, 2) of normal, patient-derived cells, and CRISPR-modified cells (knock-out #3, #5, and knock-in #203) were incubated in 2% low serum medium at 37° C. with 5% $CO_2$ and 3% $O_2$ for 5 days and were performed for ALP staining to detect alkaline phosphatase, expressed in early osteogenic differentiation (FIG. 5*a*), and normal, patient-derived cells, and CRISPR-modified cells were maintained in 2% low serum medium without or with BMP2 or BMP4 (50 ng/ml) for 21 days and followed by Alizarin Red S staining to sense calcium deposits in late osteogenic differentiation (FIG. 5*b*).
Figure 5B:
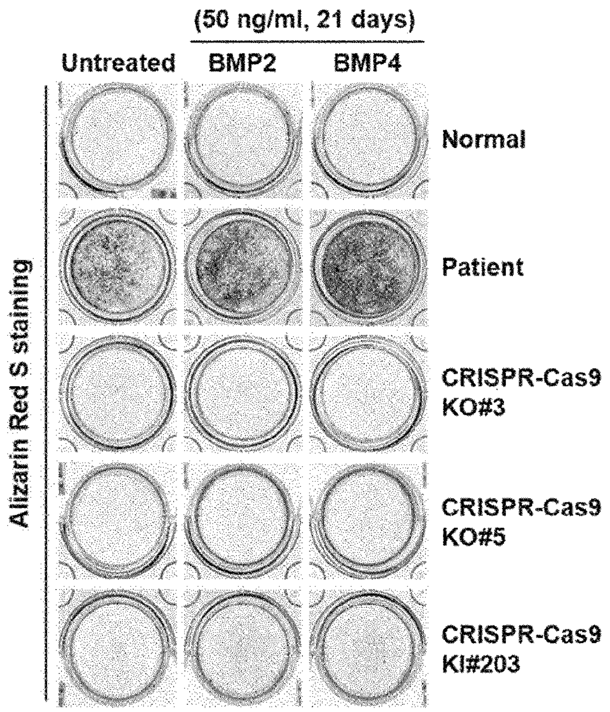

<210> SEQ ID NO 62
<211> LENGTH: 35
<212> TYPE: DNA
<213> ORGANISM: Artificial Sequence
<220> FEATURE:
<223> OTHER INFORMATION: FIG. 4a_mutant allele

<400> SEQUENCE: 62
ggaagataat gcagccataa gcaaggtgag tgtat 35

<210> SEQ ID NO 63
<211> LENGTH: 35
<212> TYPE: DNA
<213> ORGANISM: Artificial Sequence
<220> FEATURE:
<223> OTHER INFORMATION: FIG. 4a_Donor template

<400> SEQUENCE: 63
ggaagataat gcagccatct ccgaggtgag tgtat 35

<210> SEQ ID NO 64
<211> LENGTH: 35
<212> TYPE: DNA
<213> ORGANISM: Artificial Sequence
<220> FEATURE:
<223> OTHER INFORMATION: FIG. 4a_Corrected template

<400> SEQUENCE: 64
ggaagataat gcagccatct ccgaggtgag tgtat 35

Figure 4B:
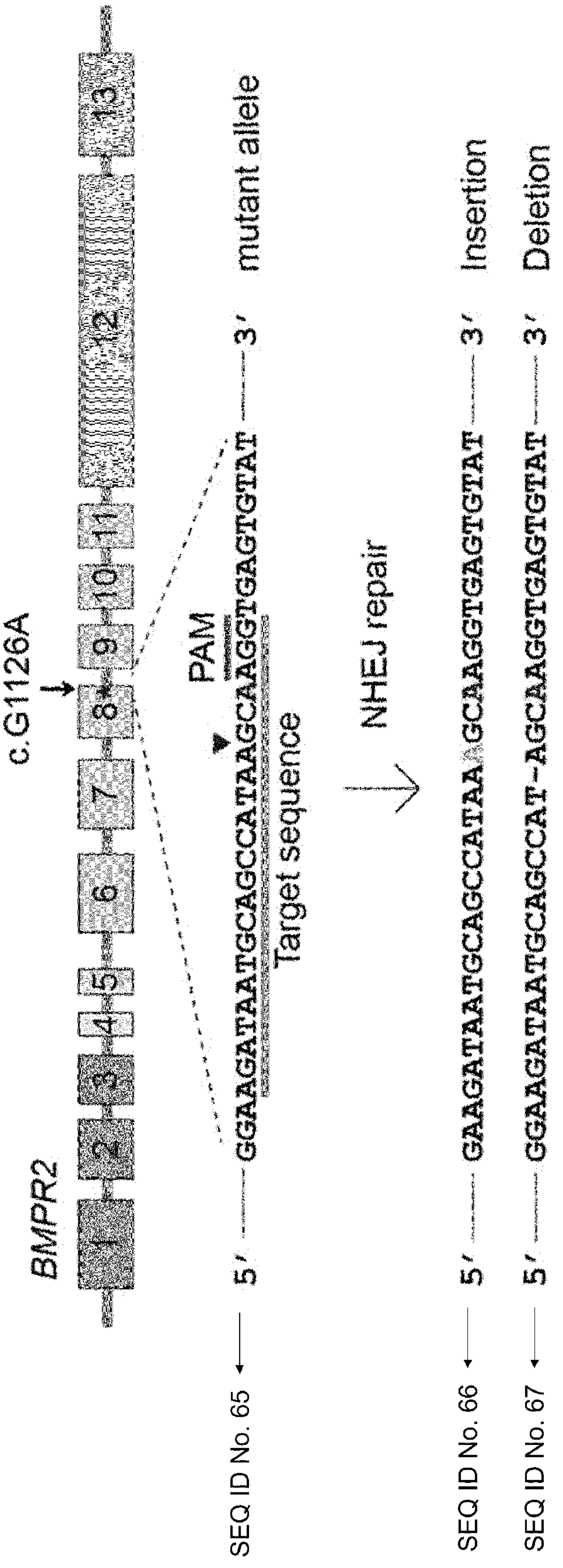
Figure 4C:
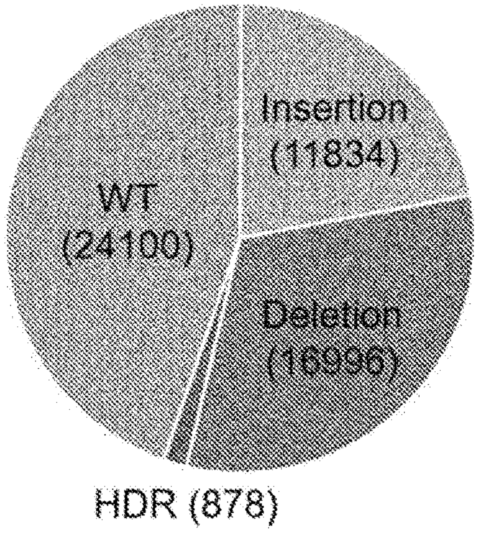

<210> SEQ ID NO 65
<211> LENGTH: 35
<212> TYPE: DNA
<213> ORGANISM: Artificial Sequence
<220> FEATURE:
<223> OTHER INFORMATION: FIG. 4b_mutant allele

<400> SEQUENCE: 65
ggaagataat gcagccataa gcaaggtgag tgtat 35

<210> SEQ ID NO 66
<211> LENGTH: 35
<212> TYPE: DNA
<213> ORGANISM: Artificial Sequence
<220> FEATURE:
<223> OTHER INFORMATION: FIG. 4b_Insertion

<400> SEQUENCE: 66
gaagataatg cagccataaa gcaaggtgag tgtat 35

<210> SEQ ID NO 67
<211> LENGTH: 35
<212> TYPE: DNA
<213> ORGANISM: Artificial Sequence
<220> FEATURE:
<223> OTHER INFORMATION: FIG. 4b_Deletion
<220> FEATURE:
<221> NAME/KEY: misc_difference
<222> LOCATION: (19)..(19)
<223> OTHER INFORMATION: replace= "-" for a deletion

<400> SEQUENCE: 67
ggaagataat gcagccataa gcaaggtgag tgtat 35

<210> SEQ ID NO 68
<211> LENGTH: 1038
<212> TYPE: PRT
<213> ORGANISM: Artificial Sequence
<220> FEATURE:
<223> OTHER INFORMATION: Human BMPR2

<400> SEQUENCE: 68

Met Thr Ser Ser Leu Gln Arg Pro Trp Arg Val Pro Trp Leu Pro Trp

-continued

```
1               5                   10                  15

Thr Ile Leu Leu Val Ser Thr Ala Ala Ala Ser Gln Asn Gln Glu Arg
            20                  25                  30

Leu Cys Ala Phe Lys Asp Pro Tyr Gln Gln Asp Leu Gly Ile Gly Glu
        35                  40                  45

Ser Arg Ile Ser His Glu Asn Gly Thr Ile Leu Cys Ser Lys Gly Ser
    50                  55                  60

Thr Cys Tyr Gly Leu Trp Glu Lys Ser Lys Gly Asp Ile Asn Leu Val
65                  70                  75                  80

Lys Gln Gly Cys Trp Ser His Ile Gly Asp Pro Gln Glu Cys His Tyr
                85                  90                  95

Glu Glu Cys Val Val Thr Thr Thr Pro Pro Ser Ile Gln Asn Gly Thr
            100                 105                 110

Tyr Arg Phe Cys Cys Cys Ser Thr Asp Leu Cys Asn Val Asn Phe Thr
        115                 120                 125

Glu Asn Phe Pro Pro Pro Asp Thr Thr Pro Leu Ser Pro Pro His Ser
    130                 135                 140

Phe Asn Arg Asp Glu Thr Ile Ile Ile Ala Leu Ala Ser Val Ser Val
145                 150                 155                 160

Leu Ala Val Leu Ile Val Ala Leu Cys Phe Gly Tyr Arg Met Leu Thr
                165                 170                 175

Gly Asp Arg Lys Gln Gly Leu His Ser Met Asn Met Met Glu Ala Ala
            180                 185                 190

Ala Ser Glu Pro Ser Leu Asp Leu Asp Asn Leu Lys Leu Leu Glu Leu
        195                 200                 205

Ile Gly Arg Gly Arg Tyr Gly Ala Val Tyr Lys Gly Ser Leu Asp Glu
    210                 215                 220

Arg Pro Val Ala Val Lys Val Phe Ser Phe Ala Asn Arg Gln Asn Phe
225                 230                 235                 240

Ile Asn Glu Lys Asn Ile Tyr Arg Val Pro Leu Met Glu His Asp Asn
                245                 250                 255

Ile Ala Arg Phe Ile Val Gly Asp Glu Arg Val Thr Ala Asp Gly Arg
            260                 265                 270

Met Glu Tyr Leu Leu Val Met Glu Tyr Tyr Pro Asn Gly Ser Leu Cys
        275                 280                 285

Lys Tyr Leu Ser Leu His Thr Ser Asp Trp Val Ser Ser Cys Arg Leu
    290                 295                 300

Ala His Ser Val Thr Arg Gly Leu Ala Tyr Leu His Thr Glu Leu Pro
305                 310                 315                 320

Arg Gly Asp His Tyr Lys Pro Ala Ile Ser His Arg Asp Leu Asn Ser
                325                 330                 335

Arg Asn Val Leu Val Lys Asn Asp Gly Thr Cys Val Ile Ser Asp Phe
            340                 345                 350

Gly Leu Ser Met Arg Leu Thr Gly Asn Arg Leu Val Arg Pro Gly Glu
        355                 360                 365

Glu Asp Asn Ala Ala Ile Ser Glu Val Gly Thr Ile Arg Tyr Met Ala
    370                 375                 380

Pro Glu Val Leu Glu Gly Ala Val Asn Leu Arg Asp Cys Glu Ser Ala
385                 390                 395                 400

Leu Lys Gln Val Asp Met Tyr Ala Leu Gly Leu Ile Tyr Trp Glu Ile
                405                 410                 415

Phe Met Arg Cys Thr Asp Leu Phe Pro Gly Glu Ser Val Pro Glu Tyr
            420                 425                 430
```

-continued

```
Gln Met Ala Phe Gln Thr Glu Val Gly Asn His Pro Thr Phe Glu Asp
        435                 440                 445

Met Gln Val Leu Val Ser Arg Glu Lys Gln Arg Pro Lys Phe Pro Glu
    450                 455                 460

Ala Trp Lys Glu Asn Ser Leu Ala Val Arg Ser Leu Lys Glu Thr Ile
465                 470                 475                 480

Glu Asp Cys Trp Asp Gln Asp Ala Glu Ala Arg Leu Thr Ala Gln Cys
                485                 490                 495

Ala Glu Glu Arg Met Ala Glu Leu Met Met Ile Trp Glu Arg Asn Lys
            500                 505                 510

Ser Val Ser Pro Thr Val Asn Pro Met Ser Thr Ala Met Gln Asn Glu
        515                 520                 525

Arg Asn Leu Ser His Asn Arg Arg Val Pro Lys Ile Gly Pro Tyr Pro
    530                 535                 540

Asp Tyr Ser Ser Ser Ser Tyr Ile Glu Asp Ser Ile His His Thr Asp
545                 550                 555                 560

Ser Ile Val Lys Asn Ile Ser Ser Glu His Ser Met Ser Ser Thr Pro
                565                 570                 575

Leu Thr Ile Gly Glu Lys Asn Arg Asn Ser Ile Asn Tyr Glu Arg Gln
            580                 585                 590

Gln Ala Gln Ala Arg Ile Pro Ser Pro Glu Thr Ser Val Thr Ser Leu
        595                 600                 605

Ser Thr Asn Thr Thr Thr Thr Asn Thr Thr Gly Leu Thr Pro Ser Thr
    610                 615                 620

Gly Met Thr Thr Ile Ser Glu Met Pro Tyr Pro Asp Glu Thr Asn Leu
625                 630                 635                 640

His Thr Thr Asn Val Ala Gln Ser Ile Gly Pro Thr Pro Val Cys Leu
                645                 650                 655

Gln Leu Thr Glu Glu Asp Leu Glu Thr Asn Lys Leu Asp Pro Lys Glu
            660                 665                 670

Val Asp Lys Asn Leu Lys Glu Ser Ser Asp Glu Asn Leu Met Glu His
        675                 680                 685

Ser Leu Lys Gln Phe Ser Gly Pro Asp Pro Leu Ser Ser Thr Ser Ser
    690                 695                 700

Ser Leu Leu Tyr Pro Leu Ile Lys Leu Ala Val Glu Ala Thr Gly Gln
705                 710                 715                 720

Gln Asp Phe Thr Gln Thr Ala Asn Gly Gln Ala Cys Leu Ile Pro Asp
                725                 730                 735

Val Leu Pro Thr Gln Ile Tyr Pro Leu Pro Lys Gln Gln Asn Leu Pro
            740                 745                 750

Lys Arg Pro Thr Ser Leu Pro Leu Asn Thr Lys Asn Ser Thr Lys Glu
        755                 760                 765

Pro Arg Leu Lys Phe Gly Ser Lys His Lys Ser Asn Leu Lys Gln Val
    770                 775                 780

Glu Thr Gly Val Ala Lys Met Asn Thr Ile Asn Ala Ala Glu Pro His
785                 790                 795                 800

Val Val Thr Val Thr Met Asn Gly Val Ala Gly Arg Asn His Ser Val
                805                 810                 815

Asn Ser His Ala Ala Thr Thr Gln Tyr Ala Asn Gly Thr Val Leu Ser
            820                 825                 830

Gly Gln Thr Thr Asn Ile Val Thr His Arg Ala Gln Glu Met Leu Gln
        835                 840                 845
```

Asn Gln Phe Ile Gly Glu Asp Thr Arg Leu Asn Ile Asn Ser Ser Pro
850 855 860

Asp Glu His Glu Pro Leu Leu Arg Arg Glu Gln Gln Ala Gly His Asp
865 870 875 880

Glu Gly Val Leu Asp Arg Leu Val Asp Arg Arg Glu Arg Pro Leu Glu
885 890 895

Gly Gly Arg Thr Asn Ser Asn Asn Asn Asn Ser Asn Pro Cys Ser Glu
900 905 910

Gln Asp Val Leu Ala Gln Gly Val Pro Ser Thr Ala Ala Asp Pro Gly
915 920 925

Pro Ser Lys Pro Arg Arg Ala Gln Arg Pro Asn Ser Leu Asp Leu Ser
930 935 940

Ala Thr Asn Val Leu Asp Gly Ser Ser Ile Gln Ile Gly Glu Ser Thr
945 950 955 960

Gln Asp Gly Lys Ser Gly Ser Gly Glu Lys Ile Lys Lys Arg Val Lys
965 970 975

Thr Pro Tyr Ser Leu Lys Arg Trp Arg Pro Ser Thr Trp Val Ile Ser
980 985 990

Thr Glu Ser Leu Asp Cys Glu Val Asn Asn Asn Gly Ser Asn Arg Ala
995 1000 1005

Val His Ser Lys Ser Ser Thr Ala Val Tyr Leu Ala Glu Gly Gly Thr
1010 1015 1020

Ala Thr Thr Met Val Ser Lys Asp Ile Gly Met Asn Cys Leu
1025 1030 1035

<210> SEQ ID NO 69
<211> LENGTH: 509
<212> TYPE: PRT
<213> ORGANISM: Artificial Sequence
<220> FEATURE:
<223> OTHER INFORMATION: Human ACVR1

<400> SEQUENCE: 69

Met Val Asp Gly Val Met Ile Leu Pro Val Leu Ile Met Ile Ala Leu
1 5 10 15

Pro Ser Pro Ser Met Glu Asp Glu Lys Pro Lys Val Asn Pro Lys Leu
20 25 30

Tyr Met Cys Val Cys Glu Gly Leu Ser Cys Gly Asn Glu Asp His Cys
35 40 45

Glu Gly Gln Gln Cys Phe Ser Ser Leu Ser Ile Asn Asp Gly Phe His
50 55 60

Val Tyr Gln Lys Gly Cys Phe Gln Val Tyr Glu Gln Gly Lys Met Thr
65 70 75 80

Cys Lys Thr Pro Pro Ser Pro Gly Gln Ala Val Glu Cys Cys Gln Gly
85 90 95

Asp Trp Cys Asn Arg Asn Ile Thr Ala Gln Leu Pro Thr Lys Gly Lys
100 105 110

Ser Phe Pro Gly Thr Gln Asn Phe His Leu Glu Val Gly Leu Ile Ile
115 120 125

Leu Ser Val Val Phe Ala Val Cys Leu Leu Ala Cys Leu Leu Gly Val
130 135 140

Ala Leu Arg Lys Phe Lys Arg Arg Asn Gln Glu Arg Leu Asn Pro Arg
145 150 155 160

Asp Val Glu Tyr Gly Thr Ile Glu Gly Leu Ile Thr Thr Asn Val Gly
165 170 175

-continued

```
Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
    450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505
```

The invention claimed is:

1. A mutation complex comprising a BMPR2 (SEQ ID No. 68)-E376K mutant in which an amino acid 376 of a human bone morphogenetic protein type 2 receptor (BMPR2) (SEQ ID No. 68) gene encoding BMPR2 (SEQ ID No. 68) is mutated from glutamic acid (E) to lysine (K) and an ACVR1 (SEQ ID No. 69)-R206H mutant in which an amino acid 206 of a human activin A type I receptor (ACVR1) (SEQ ID No. 69) gene encoding ACVR1 is mutated from arginine (R) to histidine (H).

2. The mutation complex of claim 1, wherein the mutation complex is characterized by having an additive effect to osteogenic differentiation by binding and expressing the BMPR2-E376K mutant and the ACVR1-R206H mutant.

3. The mutation complex of claim 1, wherein the mutation complex is characterized by being used to treat bone disease through osteogenic differentiation.

4. A cell line including the mutant of claim 1.

* * * * *